US012245870B2

(12) United States Patent
Javed et al.

(10) Patent No.: US 12,245,870 B2
(45) Date of Patent: Mar. 11, 2025

(54) METHODS AND APPARATUS FOR MONITORING CHRONIC DISEASE

(71) Applicant: RESMED SENSOR TECHNOLOGIES LIMITED, Clonskeagh (IE)

(72) Inventors: Faizan Javed, Sydney (AU); Steven Paul Farrugia, Sydney (AU)

(73) Assignee: ResMed Sensor Technologies Limited, Dublin (IE)

( * ) Notice: Subject to any disclaimer, the term of this patent is extended or adjusted under 35 U.S.C. 154(b) by 668 days.

(21) Appl. No.: 17/301,786

(22) Filed: Apr. 14, 2021

(65) Prior Publication Data
US 2021/0298666 A1 Sep. 30, 2021

Related U.S. Application Data

(63) Continuation of application No. 15/313,225, filed as application No. PCT/AU2015/050273 on May 25, 2015, now Pat. No. 10,980,476.

(30) Foreign Application Priority Data

May 26, 2014 (AU) .................. 2014901975

(51) Int. Cl.
*A61B 5/08* (2006.01)
*A61B 5/00* (2006.01)
(Continued)

(52) U.S. Cl.
CPC .............. *A61B 5/4842* (2013.01); *A61B 5/08* (2013.01); *A61B 5/0816* (2013.01); *A61B 5/087* (2013.01);
(Continued)

(58) Field of Classification Search
CPC ......... A61B 5/08; A61B 5/0816; A61B 5/087; A61B 5/113; A61B 5/4818; A61B 5/4842;
(Continued)

(56) References Cited

U.S. PATENT DOCUMENTS 4,944,310 A 7/1990 Sullivan
5,732,696 A 3/1998 Rapoport et al.
(Continued)

FOREIGN PATENT DOCUMENTS

JP 2004113340 A 4/2004
JP 2006502774 A 1/2006
(Continued)

OTHER PUBLICATIONS

Extended European search report for Application No. EP22155706 dated May 25, 2022.
(Continued)

*Primary Examiner* — Eric J Messersmith
(74) *Attorney, Agent, or Firm* — Botos Churchill IP Law LLP

(57) ABSTRACT

A method and apparatus monitors chronic disease state of a patient. The method may include extracting, in a processor, for each of a plurality of monitoring sessions, a respiratory feature from a respiratory signal indicative of the patient's respiration during the monitoring session, the respiratory signal derived from at least one sensor; and computing, in a processor, a stability measure of the patient for a monitoring session, the stability measure representing an indication of a change point having occurred at the monitoring session in a statistical distribution of the respiratory feature.

18 Claims, 19 Drawing Sheets

(51) Int. Cl.
   *A61B 5/087*  (2006.01)
   *A61B 5/113*  (2006.01)
   *A61M 16/00*  (2006.01)
(52) U.S. Cl.
   CPC ............ *A61B 5/113* (2013.01); *A61B 5/4818* (2013.01); *A61B 5/486* (2013.01); *A61B 5/7275* (2013.01); *A61B 5/7282* (2013.01); *A61B 5/746* (2013.01); *A61M 16/0069* (2014.02); *A61M 2230/63* (2013.01)
(58) Field of Classification Search
   CPC ..... A61B 5/486; A61B 5/7275; A61B 5/7282; A61B 5/746; A61M 16/0069; A61M 2230/63
   See application file for complete search history.

(56) References Cited

U.S. PATENT DOCUMENTS

| | | | |
|---|---|---|---|
| 6,532,959 | B1 | 3/2003 | Berthon-Jones |
| 7,297,113 | B1 | 11/2007 | Russell et al. |
| 8,454,528 | B2 * | 6/2013 | Yuen .................. A61B 5/0205 600/407 |
| 2005/0020932 | A1 | 1/2005 | Haberland et al. |
| 2008/0177789 | A1 | 7/2008 | Stoval |
| 2011/0009753 | A1 * | 1/2011 | Zhang .................. A61B 5/0816 600/529 |
| 2011/0077532 | A1 | 3/2011 | Kim et al. |
| 2011/0282216 | A1 * | 11/2011 | Shinar .................. A61B 5/4839 600/483 |
| 2011/0306846 | A1 | 12/2011 | Osorio |
| 2013/0340758 | A1 * | 12/2013 | Schindhelm ........... G16H 50/20 128/204.23 |
| 2017/0071484 | A1 | 3/2017 | Strachan et al. |

FOREIGN PATENT DOCUMENTS

| | | |
|---|---|---|
| JP | 2007500046 A | 1/2007 |
| JP | 2009532072 A | 9/2009 |
| JP | 2011510784 A | 4/2011 |
| JP | 2012000211 A | 1/2012 |
| JP | 2012532668 A | 12/2012 |
| WO | 2009098627 A1 | 8/2009 |
| WO | 2010066008 A1 | 6/2010 |
| WO | 2013144827 A1 | 10/2013 |
| WO | 2013177621 A1 | 12/2013 |

OTHER PUBLICATIONS

Notice of Allowance issued in corresponding Japanese Patent Application No. 2022-064446, mailed Feb. 10, 2023, 3 pages.
Office Action for Japanese Patent Application No. 2020-154741, Jul. 30, 2021.
Chinese Office Action issued in corresponding CN application No. 201580040820.6 on Dec. 26, 2018.
International Search Report for Application No. PCT/AU2015/050273 dated Aug. 27, 2015.
International Written Opinion for Application No. PCT/AU2015/050273 dated Aug. 27, 2015.
Japanese Office Action mailed Apr. 24, 2020 for JP Application No. P2016-569741.
JP Office Action issued in corresponding JP application No. P2016-569741 on Apr. 2, 2019.
Ashutosh, K , et al., "Prediction Criteria for Successful Weaning from Respiratory Support: Statistical and Connectionist Analyses" (1991). Electrical Engineering and Computer Science Technical Reports. Paper 115, whole document.
Jaehee, Kim , et al., "Bayesian multiple change-point estimation with annealing stochastic approximation Monte Carlo", Computational Statistics, vol. 25, No. 2, Jun. 1, 2010, pp. 215-239, XP055431519, DE ISSN: 0943-4062, DOI: 10.1007/s00180-009-0172-x.
Kawahara, Yoshinobu , et al., "Sequential change-point detection based on direct density-ratio estimation", Statistical Analysis and Data Mining Wiley&Sons, USA, vol. 5, No. 2, Apr. 2012 (Apr. 2012), pp. 114-127, ISSN: 1932-1864, Jun. 24, 2011, 114-127.
West John B, "Respiratory Physiology", Lippincott Williams & Wilkins, 9th edition published 2011.

* cited by examiner

METHODS AND APPARATUS FOR MONITORING CHRONIC DISEASE

1 CROSS-REFERENCE TO RELATED APPLICATIONS

This application is a continuation of U.S. patent application Ser. No. 15/313,225, filed on Nov. 22, 2016, which is a national phase entry under 35 U.S.C. § 371 of International Application No. PCT/AU2015/050273 filed May 25, 2015, published in English, which claims priority from Australian Provisional Patent Application No. 2014901975, filed May 26, 2014, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY

5.1 Field of the Technology

The present technology relates to one or more of the detection, diagnosis, treatment, prevention and amelioration of chronic disease. In particular, the present technology relates to medical devices or apparatus, and their use.

5.2 Description of the Related Art 5.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition, published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Heart failure (HF) is a relatively common and severe clinical condition, characterised by the inability of the heart to keep up with the oxygen demands of the body. Management of heart failure is a significant challenge to modern healthcare systems due to its high prevalence and severity. HF is a chronic condition, which is progressive in nature. The progression of HF is often characterized as relatively stable over long periods of time (albeit with reduced cardiovascular function) punctuated by episodes of an acute nature. In these acute episodes, the patient experiences worsening of symptoms such as dyspnea (difficulty breathing), gallop rhythms, increased jugular venous pressure, and orthopnea. This is typically accompanied by overt congestion (which is the buildup of fluid in the pulmonary cavity). This excess fluid often leads to measurable weight gain of several kilograms. In many cases, however, by the time overt congestion has occurred, there are limited options for the doctor to help restabilise the patients, and in many cases the patient requires hospitalization. In extreme cases, without timely treatment, the patient may undergo acute decompensated heart failure (ADHF) events, sometimes referred to as decompensations.

5.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a non-invasive patient interface. NIV has been used to treat CSR, OHS, COPD, MD and Chest Wall disorders.

5.2.3 Treatment Systems

The above-mentioned therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

5.2.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 $cmH_2O$. For other forms of therapy, such as the delivery of oxygen, the patient interface may not include a seal sufficient to facilitate delivery to the airways of a supply of gas at a positive pressure of about 10 $cmH_2O$.

5.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

5.2.3.3 Humidifier

Delivery of a flow of air without humidification may cause drying of airways. The use of a humidifier with a RPT device and the patient interface produces humidified gas that minimizes drying of the nasal mucosa and increases patient airway comfort. In addition in cooler climates, warm air applied generally to the face area in and about the patient interface is more comfortable than cold air.

5.2.4 Monitoring Systems

It is of interest to be able to monitor HF or COPD patients at home with a view to preventing or ameliorating potential clinical events such as HF decompensations or COPD exacerbations. Characteristics that have been proposed or used for the purpose of predicting clinical events include body weight, levels of B natriuretic peptides (BNP), nocturnal heart rate, and changes in sleeping posture. Polysomnography (PSG) is a conventional system for monitoring of cardio-pulmonary disorders. PSG typically involves the placement of 15 to 20 contact sensors on a person in order to record various bodily signals such as electroencephalography (EEG), electrocardiography (ECG), electrooculography (EOG), etc.

HF has been shown to be highly correlated with sleep disordered breathing (SDB). In particular, Cheyne-Stokes respiration (CSR) is caused in general by an instability in the body's respiratory control system, one cause of which is heart failure. The severity of CSR may be represented by a set of features that indicate the extent to which respiration during sleep resembles classic CSR, i.e. "Cheyne-Stokes-like" features. In addition, features indicative of the severity of OSA such as the Apnea/Hypopnea Index (AHI) have been shown to be independent predictors of death by, and hospitalization for, ADHF events. The values of and changes in such SDB features may contain useful information about the likelihood of ADHF events. Contact sensor modalities such as masks or oro-nasal cannulae with capability for monitoring and analysing respiratory parameters during sleep to extract SDB features have been proposed in the context of monitoring chronic cardio-pulmonary disease. Implantable sensors have also been utilised for monitoring thoracic impedance and cardiac arrhythmias to predict ADHF events.

HF monitoring systems based on the sensor modalities described above tend to be unsatisfactory as they either require good patient compliance, e.g. weight-based monitoring systems that rely on patients to record their daily weights, are wearable, which makes them unrealistic for long-term monitoring, or are invasive or obtrusive. The use of implantable devices is only feasible for a subset of HF patients eligible for such devices.

SleepMinder (ResMed Sensor Technologies Ltd, Dublin, Ireland) is a contactless bedside monitor suitable for long-term monitoring of chronic disease. SleepMinder contains a biomotion transceiver sensor operating on the principles of Doppler radar in a license-free band at 5.8 GHz at ultra-low power (less than 1 mW). SleepMinder is capable of measuring bodily movement, and in particular respiratory movement, over a distance ranging from 0.3 to 1.5 meters; in the case of two people in a bed, a combination of sophisticated sensor design and intelligent signal processing allows Sleep-Minder to measure only the respiratory movement of the person nearest to the sensor. The SleepMinder is suitable for long-term monitoring of chronic disease as it is unobtrusive and does not present significant compliance issues.

6 BRIEF SUMMARY OF THE TECHNOLOGY

The present technology is directed towards providing medical apparatus used in the monitoring of cardio-pulmonary disorders or other chronic diseases having one or more of improved comfort, cost, efficacy, ease of use and manufacturability.

A first aspect of the present technology relates to apparatus used in the monitoring of a cardio-pulmonary disorder or other chronic disease.

Another aspect of the present technology relates to methods used in the monitoring of a cardio-pulmonary disorder or other chronic disease.

One form of the present technology comprises chronic disease monitoring apparatus that extracts a respiratory feature from a respiratory signal of a patient during each monitoring session and computes a stability measure from statistical analysis of a time series formed from successive values of the respiratory feature over plural monitoring sessions. The stability measure represents an indication of a change point having occurred at the monitoring session in a statistical distribution of the respiratory feature. An alert may be generated if the stability measure meets a criterion.

Another form of the present technology comprises methods of monitoring chronic disease comprising computing a stability measure as an indication of a change point having occurred in the probability distribution of a time series formed from successive values of a respiratory feature extracted from a respiratory signal of a patient over plural monitoring sessions. The stability measure represents an indication of a change point having occurred at the monitoring session in a statistical distribution of the respiratory feature. An alert may be generated if a change point in the distribution is detected. The method of computation may be retrospective or on-line.

According to a first aspect of the present technology, there is provided a method of monitoring chronic disease state of a patient. The method comprises: extracting, in a processor, for each of a plurality of monitoring sessions, a respiratory feature from a respiratory signal indicative of the patient's respiration during the monitoring session, the respiratory signal derived from at least one sensor; and computing, in a processor, a stability measure of the patient for a monitoring session, the stability measure representing an indication of a change point having occurred at the monitoring session in a statistical distribution of the respiratory feature.

According to a second aspect, there is provided a chronic disease monitoring apparatus comprising: a sensor configured to generate a respiratory signal indicative of a patient's respiration during a monitoring session; and a processor configured to carry out a method according to the first aspect.

According to a third aspect, there is provided a method of monitoring chronic disease state of a patient. The method, carried out in one or more processors, comprises: extracting, for each of a plurality of monitoring sessions, a respiratory feature from a respiratory signal indicative of the patient's respiration during the monitoring session, the respiratory signal derived from at least one sensor; forming a time series from successive values of the respiratory feature; and computing a stability measure of the patient for a monitoring session. The stability measure represents a measure of dissimilarity of probability distributions of two sets of sub-sequences of the time series. The two sets comprise sub-sequences substantially composed of samples of the time series before and after the monitoring session respectively.

According to a fourth aspect, there is provided a chronic disease monitoring apparatus comprising: a sensor configured to generate a respiratory signal indicative of a patient's respiration during a monitoring session; and a processor configured to carry out a method according to the third aspect.

According to a fifth aspect, there is provided a method of monitoring chronic disease state of a patient. The method, carried out in one or more processors, comprises: extracting, for each of a plurality of monitoring sessions, a respiratory feature from a respiratory signal indicative of the patient's respiration during the monitoring session, the respiratory signal derived from at least one sensor; computing a stability measure of the patient for a monitoring session. The stability measure represents a probability of a change point having occurred at the monitoring session in a statistical distribution of the respiratory feature. The computing comprises: computing a posterior distribution of run length for the monitoring session given values of the respiratory feature up to and including the monitoring session; and computing a sum of values of the posterior distribution of run length.

According to a sixth aspect, there is provided a chronic disease monitoring apparatus comprising: a sensor configured to generate a respiratory signal indicative of a patient's respiration during a monitoring session; and a processor configured to carry out a method according to the fifth aspect.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Treatment Systems

FIG. 1 shows an example treatment system in accordance with one form of the present technology. A patient 1000 wearing a patient interface 3000 receives a supply of air at positive pressure from an RPT device 4000. Air from the RPT device 4000 is humidified in a humidifier 5000, and passes along an air circuit 4170 to the patient 1000.

7.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

FIG. 3 shows a patient interface in the form of a nasal mask in accordance with one form of the present technology.

7.4 RPT Device

7.5 Humidifier

Figure 5:
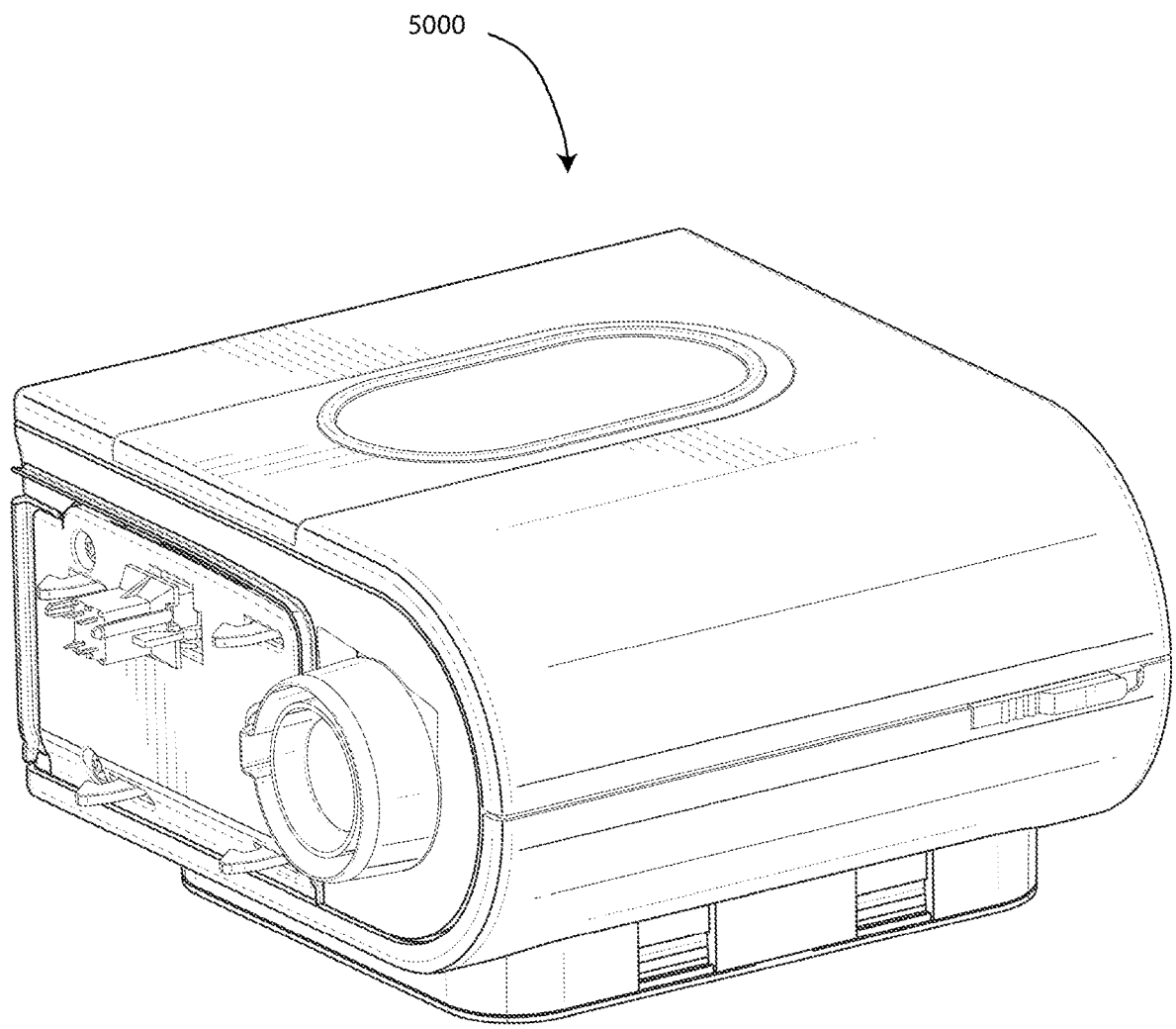

FIG. 5 shows an isometric view of a humidifier in accordance with one aspect of the present technology.

7.6 Breathing Waveforms

Figure 6A:
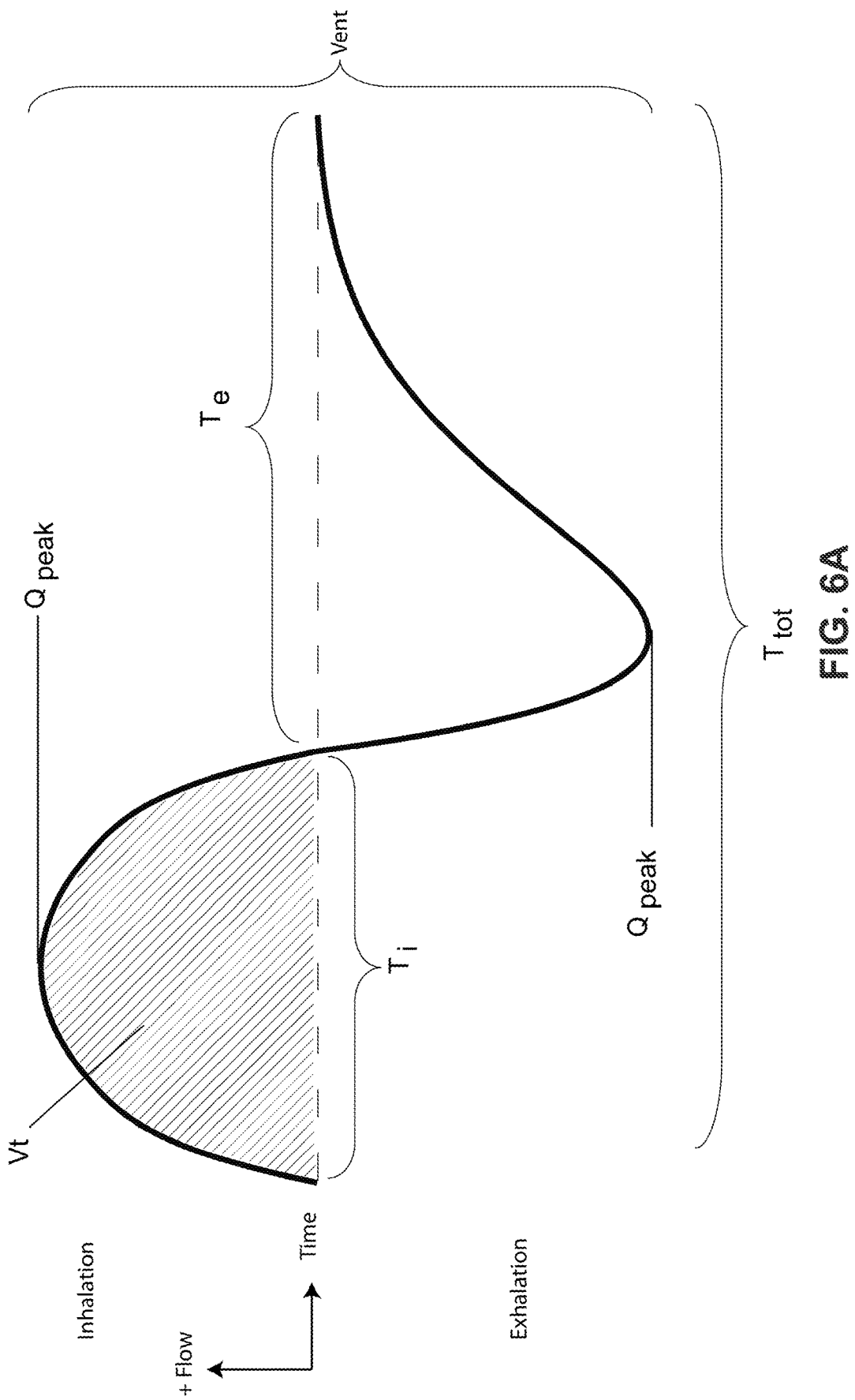

FIG. 6A shows a model typical breath waveform of a person while sleeping.

Figure 6B:
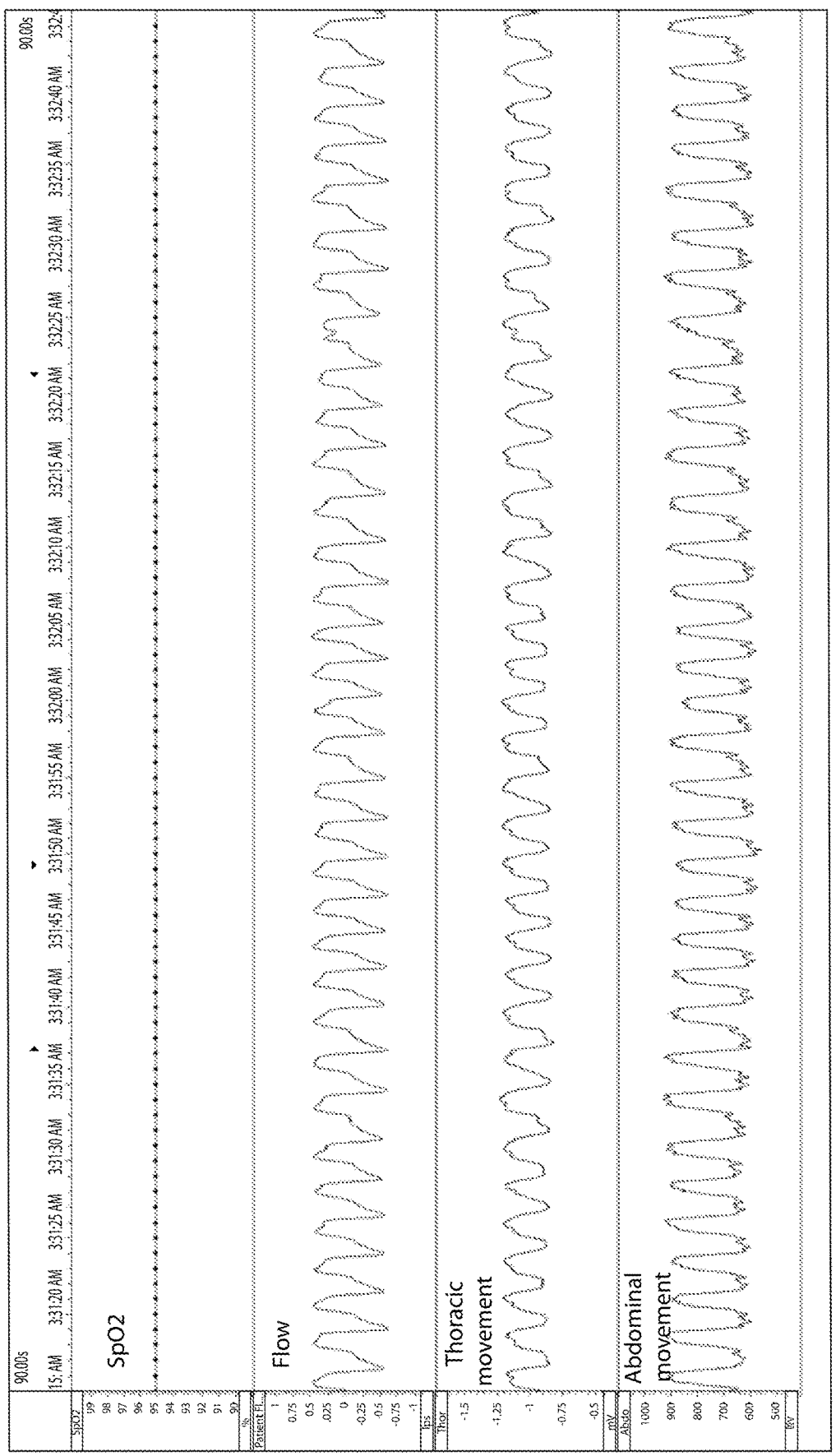

FIG. 6B shows polysomnography data of a patient during non-REM sleep breathing normally over a period of about ninety seconds.

Figure 6C:
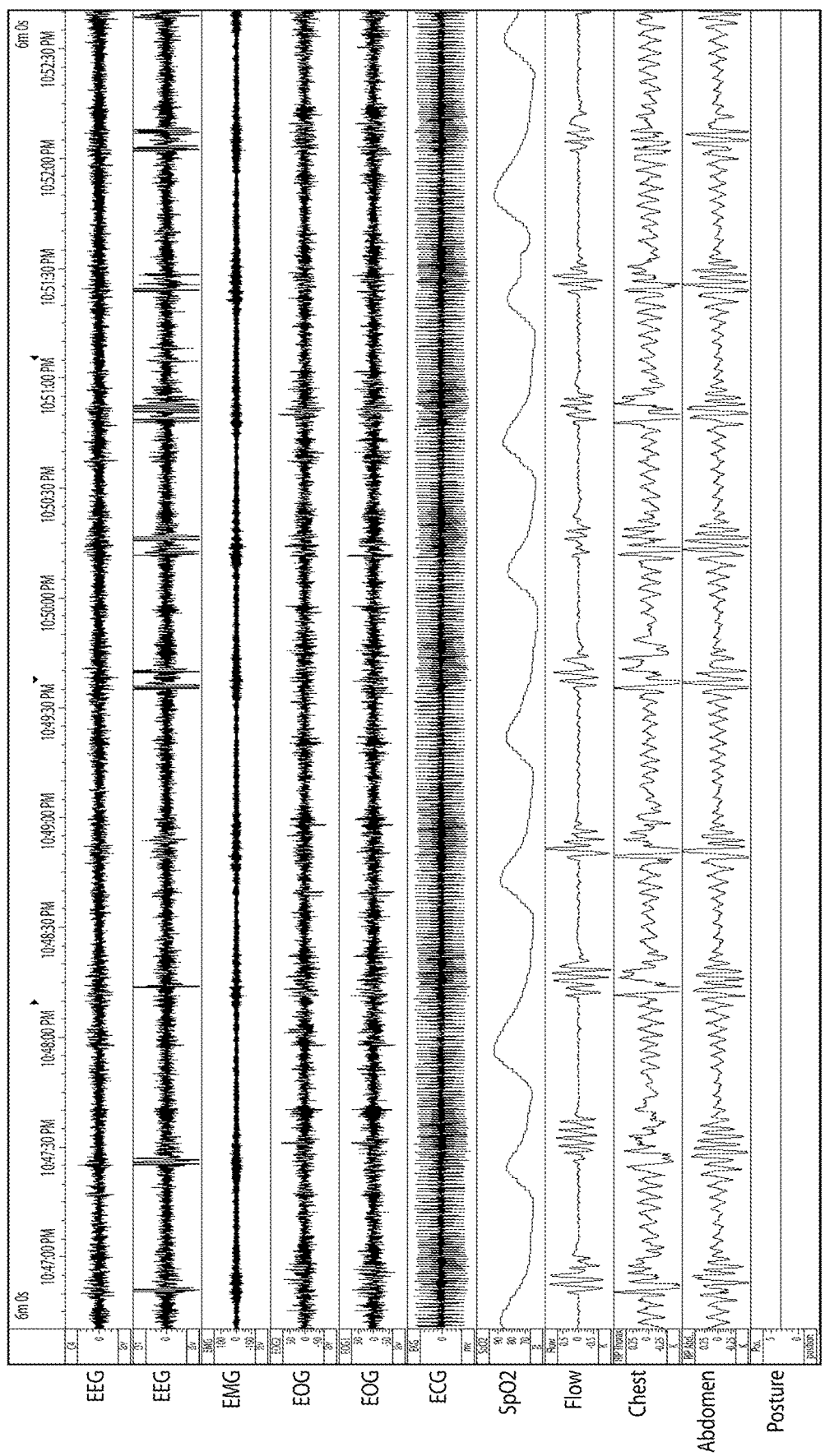

FIG. 6C shows polysomnography data of a patient with OSA.

Figure 6D:
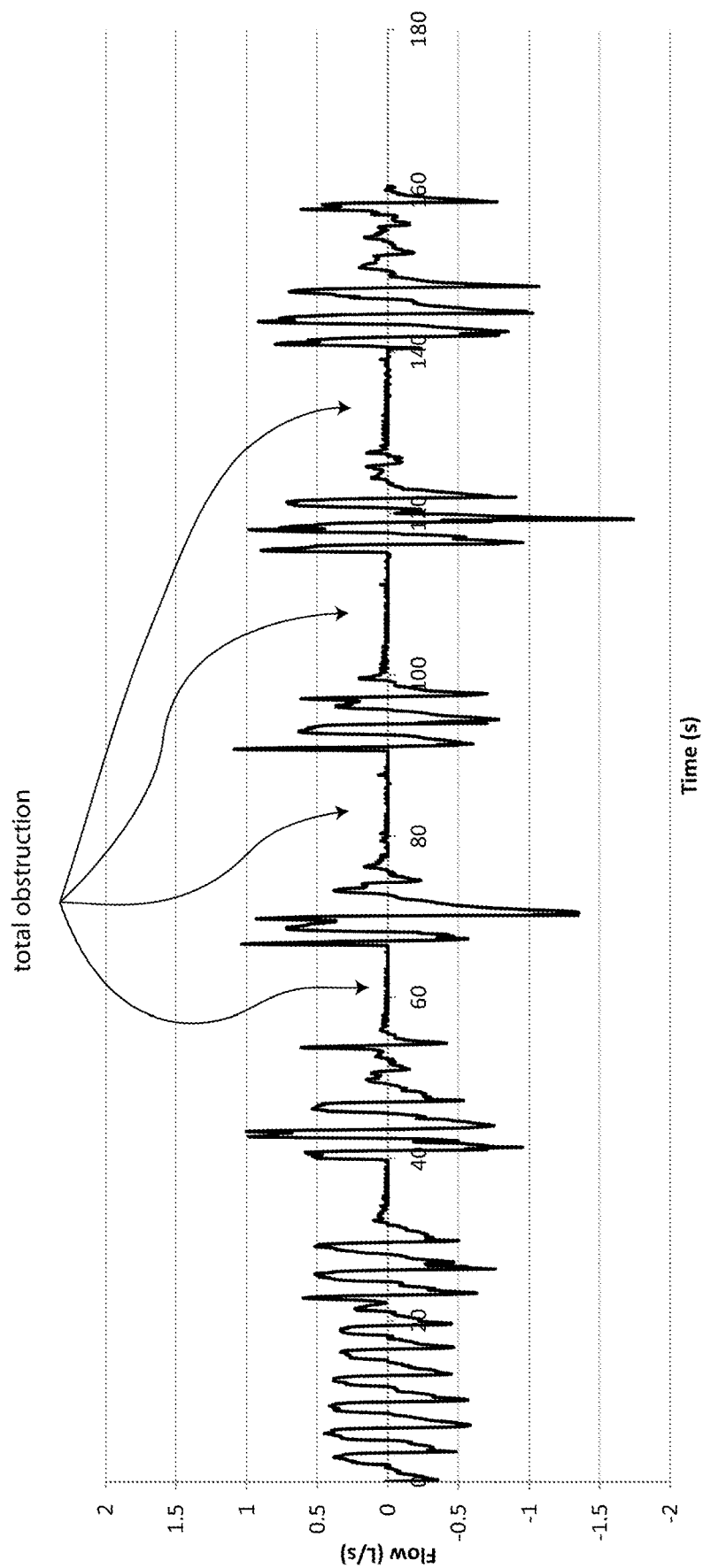

FIG. 6D shows patient flow rate data where the patient is experiencing a series of total obstructive apneas.

Figure 6E:
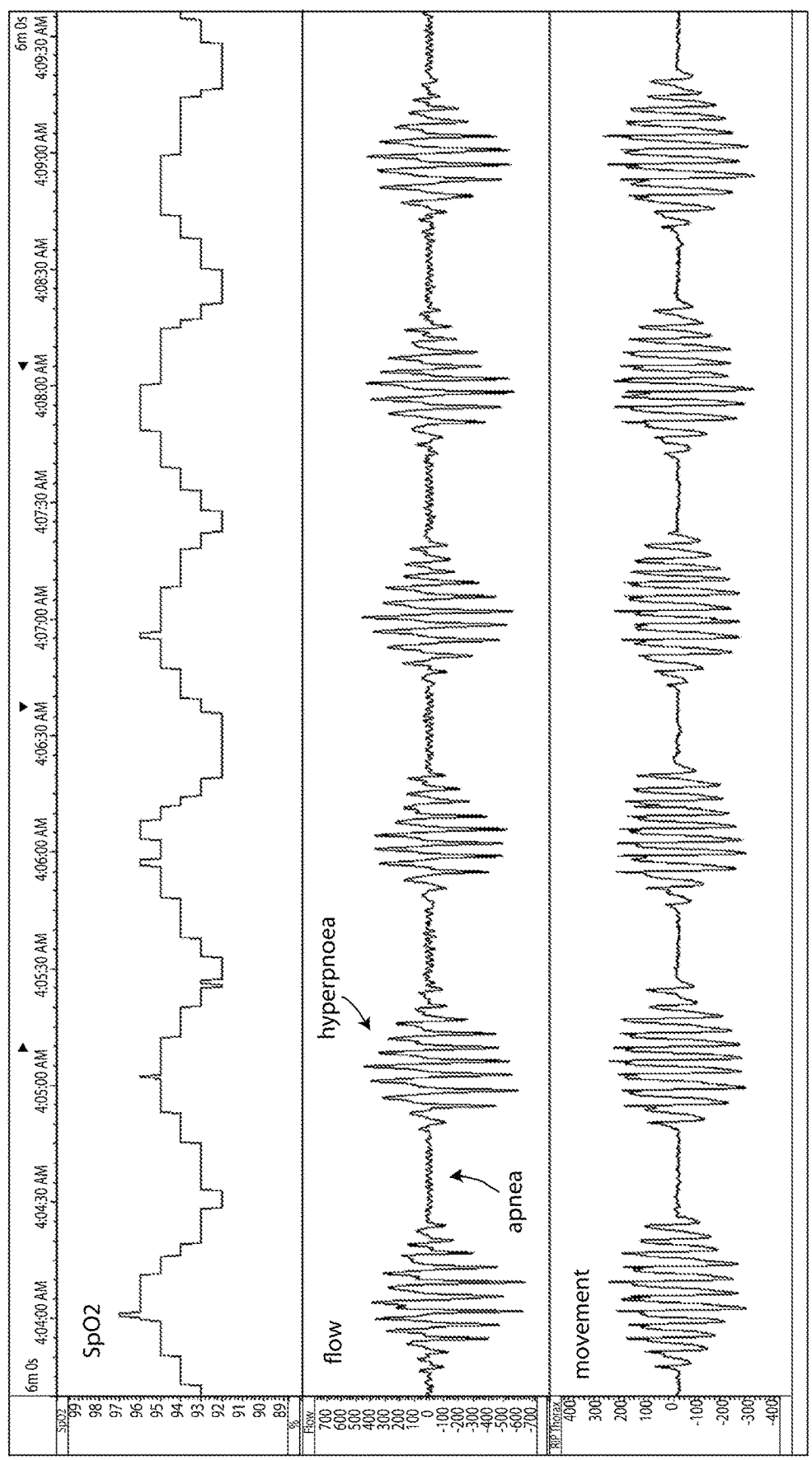

FIG. 6E shows polysomnography data of a patient with Cheyne-Stokes respiration.

7.7 Monitoring Apparatus

Figure 7A:
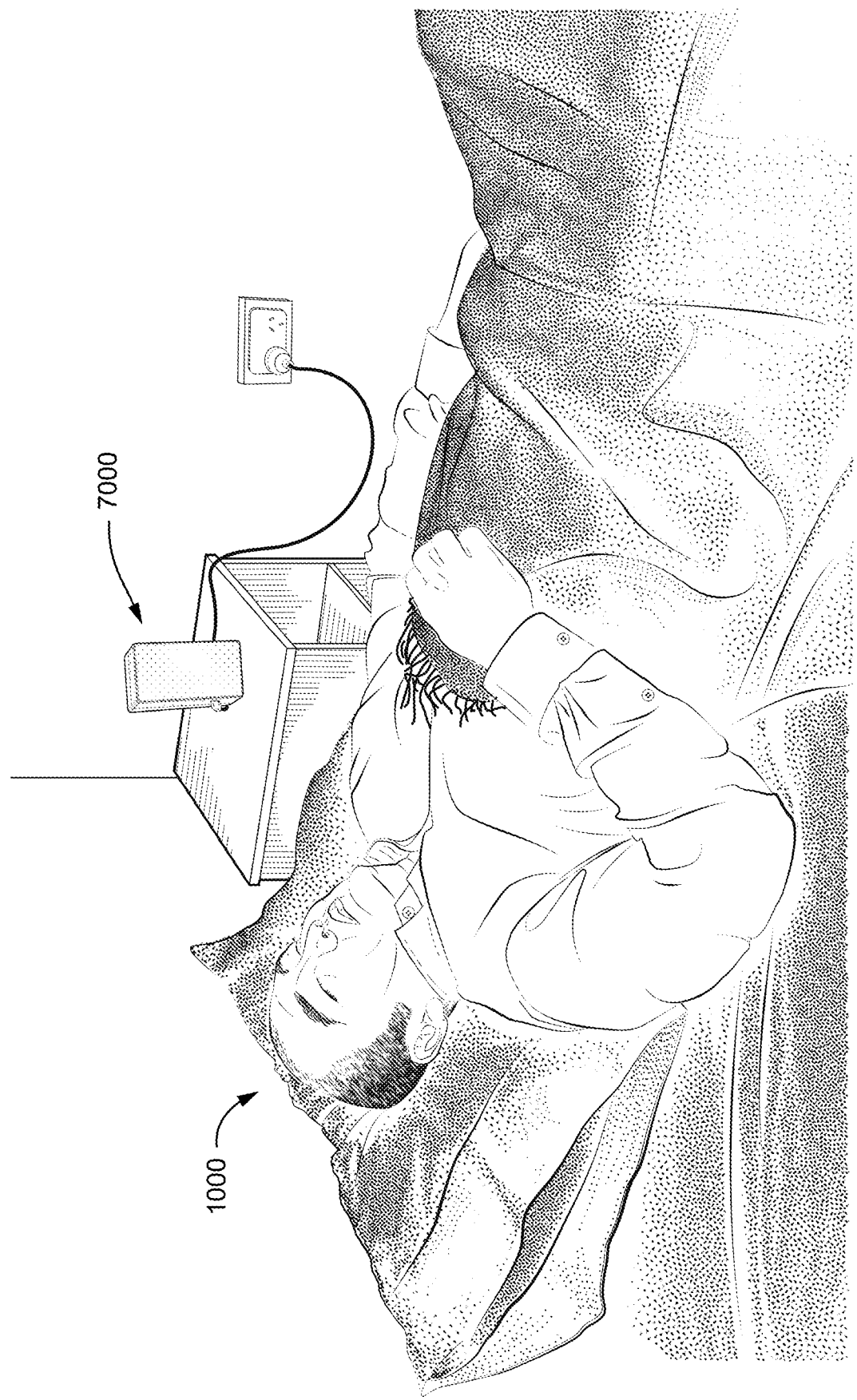

FIG. 7A shows an apparatus monitoring a sleeping patient in accordance with one form of the present technology.

Figure 7B:
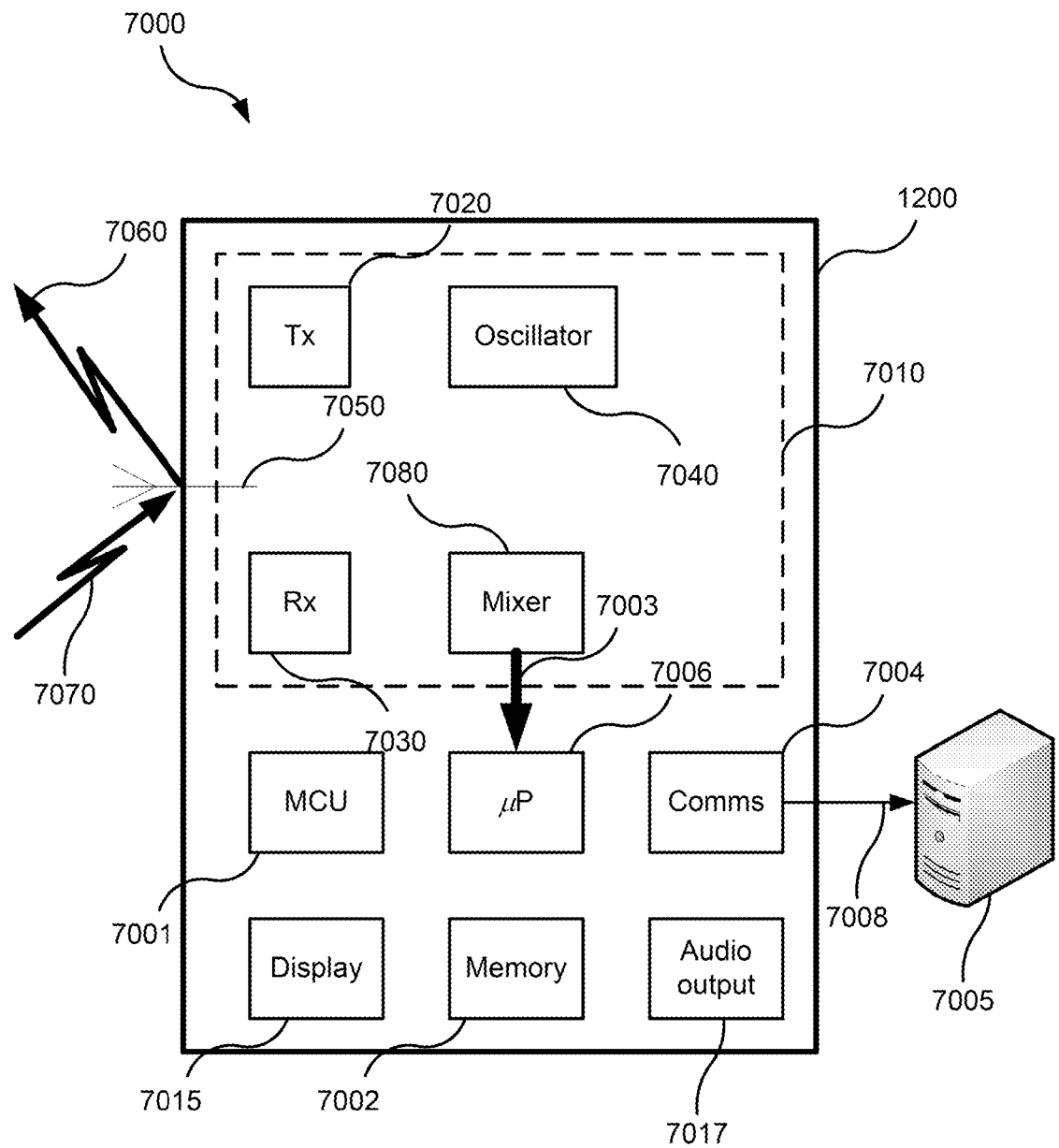

FIG. 7B is a block diagram illustrating the monitoring apparatus of FIG. 7A in more detail.

Figure 7C:
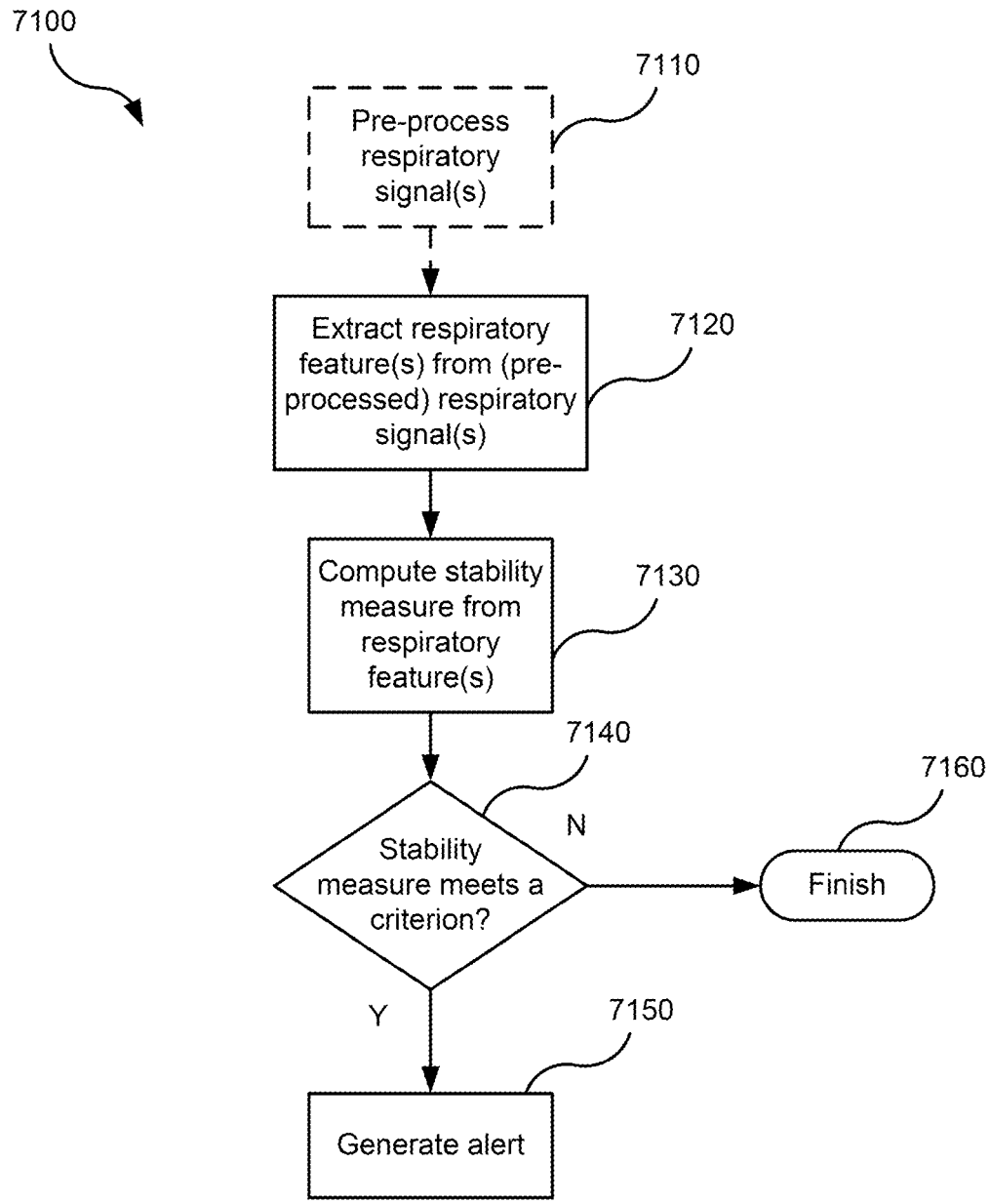

FIG. 7C is a flow chart illustrating a method of monitoring chronic disease state of a patient, as carried out by the monitoring apparatus of FIG. 7B according to one form of the present technology.

Figure 7D:
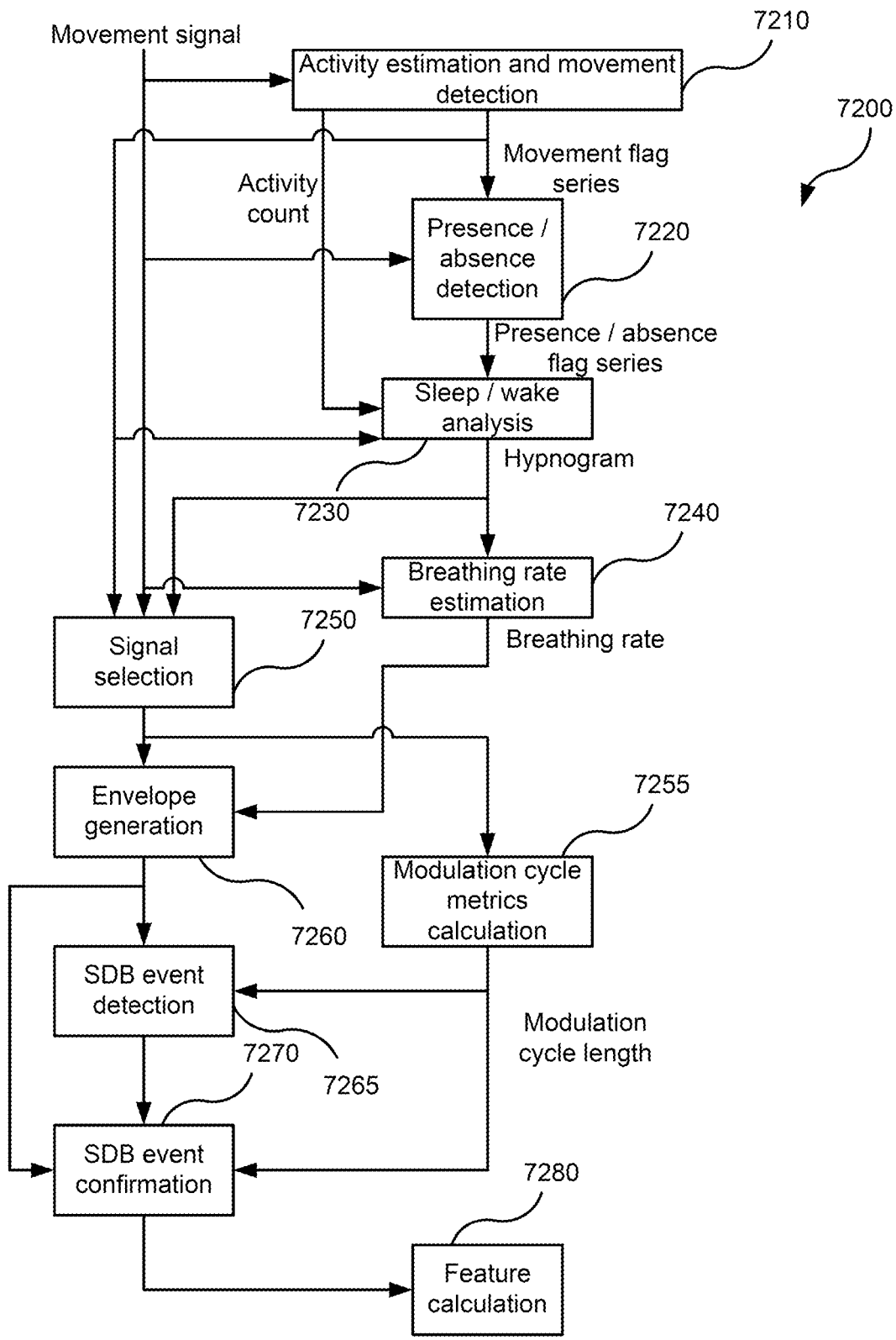

FIG. 7D is a block diagram illustrating a method that may be used to implement the feature extraction step in the method of FIG. 7C according to one form of the present technology.

Figure 7E:
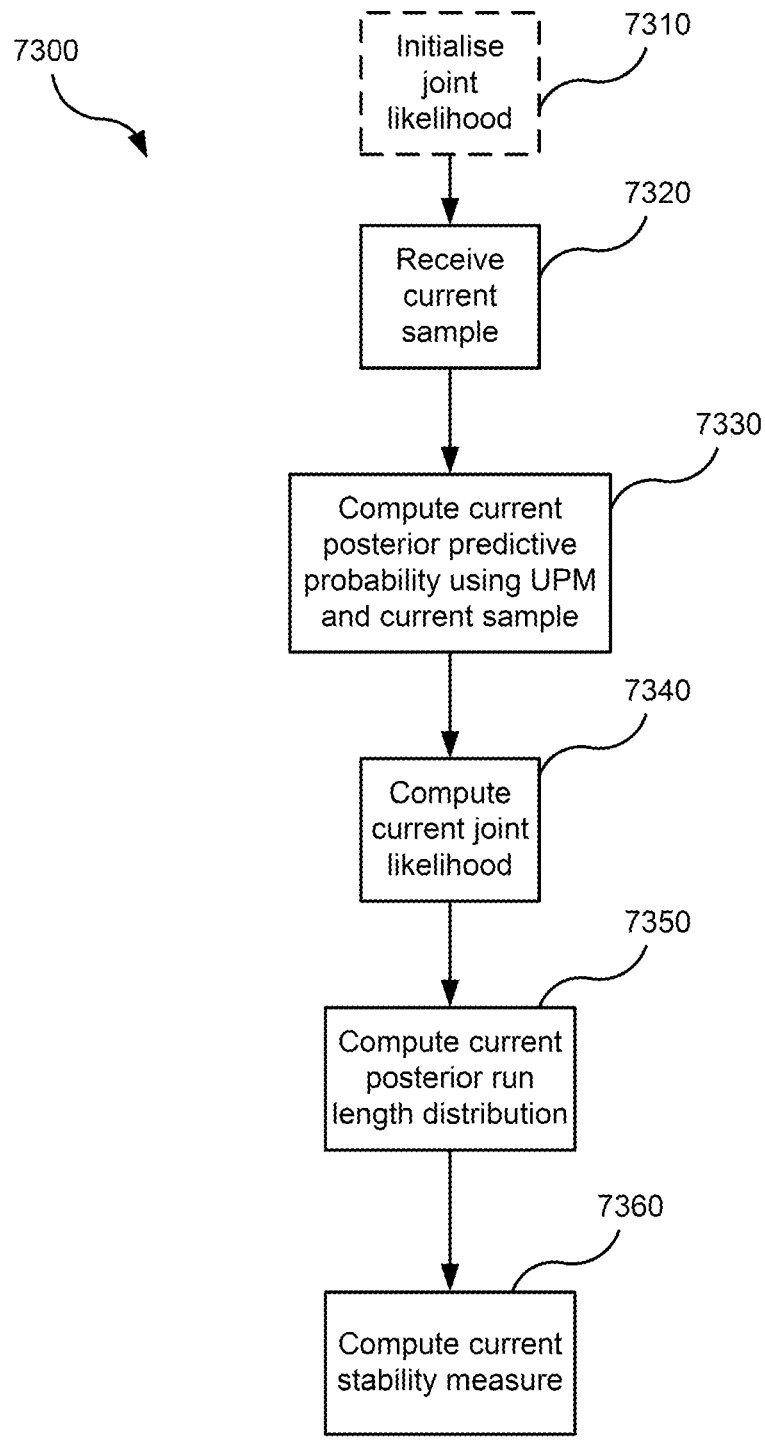

FIG. 7E is a block diagram illustrating a method that may be used to implement the stability measure computation step in the method of FIG. 7C under the on-line approach according to one form of the present technology.

Figure 7F:
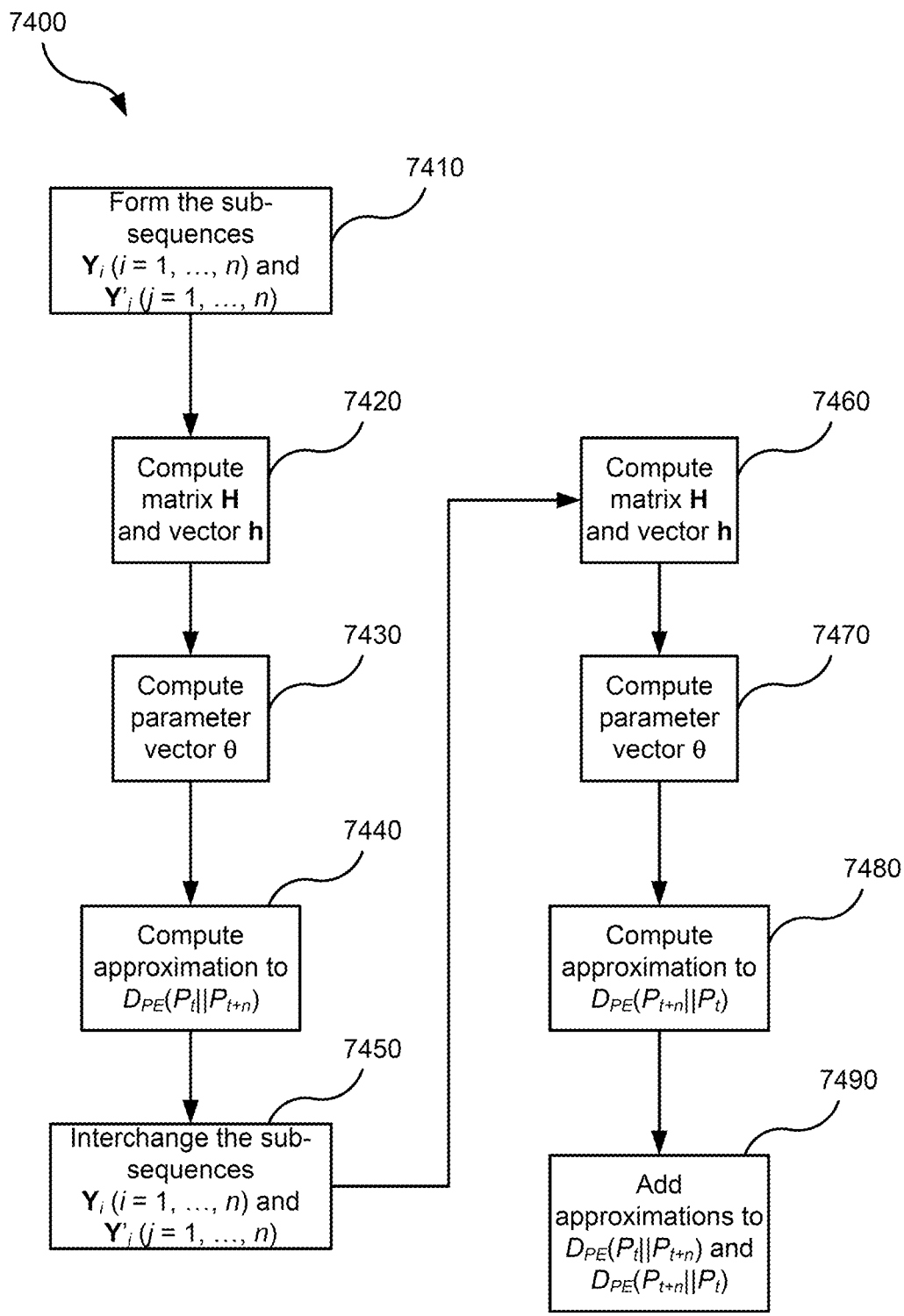

FIG. 7F is a block diagram illustrating a method that may be used to implement the stability measure computation step in the method of FIG. 7C under the retrospective approach according to one form of the present technology.

Figure 8:
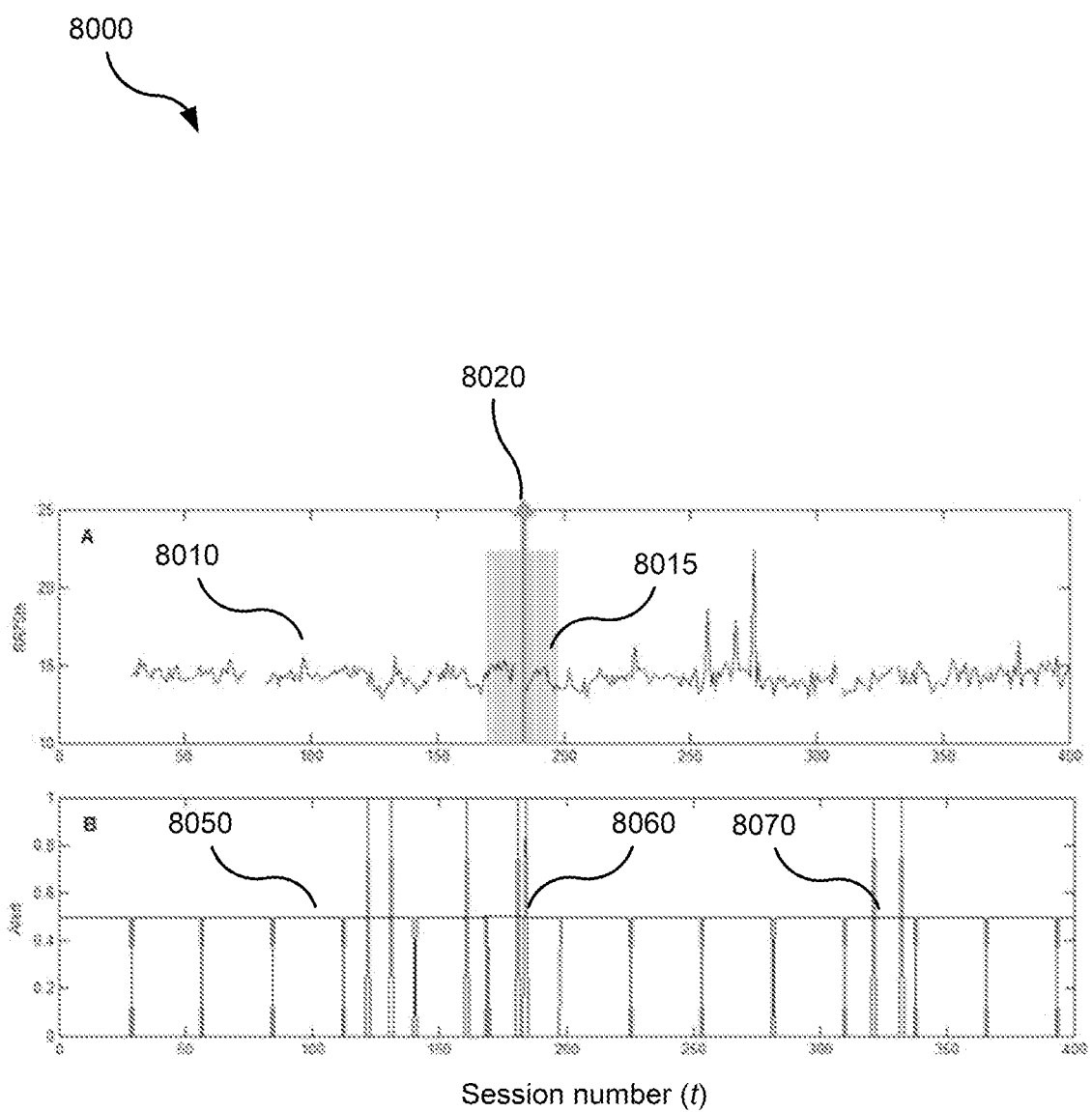

FIG. 8 contains a graph showing example results obtained from the monitoring apparatus of FIG. 7A using the method of FIG. 7C.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The apparatus and methods described below are particularly suitable for the monitoring of cardio-pulmonary health, and are described in those terms. However, the described apparatus and methods may also be applied to monitoring other chronic diseases that affect a patient's respiration.

8.1 Monitoring Apparatus and Methods

8.1.1 Unobtrusive Monitoring Apparatus

FIG. 7A illustrates an unobtrusive monitoring apparatus 7000 according to one form of the present technology. The monitoring apparatus 7000 is positioned adjacent and relatively close to the sleeping patient 1000 (e.g. on a bedside table).

FIG. 7B is a block diagram illustrating the components of the monitoring apparatus 7000 of FIG. 7A in more detail, according to one form of the present technology. In the monitoring apparatus 7000, a contactless sensor unit 1200 includes a contactless motion sensor 7010 generally directed toward the patient 1000. The motion sensor 7010 is configured to generate one or more signals representing bodily movement of the patient 1000, from which may be derived one or more respiratory movement signals representing respiratory movement of the patient.

The sensor unit 1200 may also include a microcontroller unit (MCU) 7001, and a memory 7002 (e.g. a memory card) for logging data. In one implementation, the sensor unit 1200 may include communications circuitry 7004 configured to transfer data to an external computing device 7005, e.g. a local general purpose computer, or a remote server, via a connection 7008. The connection 7008 may be wired or wireless, in which case the communications circuitry 7004 has wireless capability, and may be direct or indirect via a local network or a wide-area network (not shown) such as the Internet.

The sensor unit 1200 includes a processor 7006 configured to process the signals generated by the motion sensor 7010 as described in detail below.

The sensor unit 1200 includes a display device 7015 configured to provide visual feedback to a user. In one implementation, the display device 7015 comprises one or more warning lights (e.g., one or more light emitting diodes). The display device 7015 may also be implemented as a display screen such as an LCD or a touch-sensitive display. Operation of the display device 7015 is controlled by the processor 7006 based on an assessment of the patient's cardio-pulmonary health. The display device 7015 may be operated to show information to a user of the monitoring apparatus 7000, such as the patient 1000, or a physician or other clinician. The display device 7015 may also display a graphical user interface for operation of the monitoring apparatus 7000.

The sensor unit 1200 may also include an audio output 7017 configured to provide acoustic feedback to a user under the control of the processor 7006, e.g., a tone whose frequency varies with breathing, or an alarm which sounds when certain conditions are met.

User control of the operation of the monitoring apparatus 7000 may be based on operation of controls (not shown) that are sensed by the processor 7006 of the monitoring apparatus 7000.

One example of a sensor unit 1200 is the SleepMinder device manufactured by ResMed Sensor Technologies Ltd, which contains a contactless Doppler radio-frequency (RF) motion sensor 7010.

In one form of the present technology, such as when the SleepMinder device is used as the sensor unit 1200, the motion sensor 7010 includes an RF transmitter 7020 configured to transmit an RF signal 7060. The transmitted signal 7060 for example has the form $$s(t)=u(t)\cos(2\pi f_c t+\theta) \quad \text{(Eq. 1)}$$

In Eq. 1, the carrier frequency is $f_c$ (typically in the range 100 MHz to 100 GHz, e.g. 3 GHz to 12 GHz, e.g. 5.8 GHz or 10.5 GHz), t is time, θ is an arbitrary phase angle, and u(t) is a pulse shape. In a continuous wave system, the magnitude of u(t) may be unitary, and can be omitted from Eq. 1. More generally, the pulse u(t) may be defined as in Eq. 2:

$$u(t)=\begin{cases}1, & t\in[kT, kT+T_p], k\in Z \\ 0, & \text{otherwise}\end{cases} \quad \text{(Eq. 2)}$$

where T is the period width, and $T_p$ is the pulse width. Where $T_p \ll T$, this becomes a pulsed continuous wave system. In one case, as $T_p$ becomes very small, the spectrum of the emitted signal becomes very wide, and the system is referred to as an ultra-wideband (UWB) radar or impulse radar. Alternatively, the carrier frequency of the RF transmitted signal 7060 can be varied (chirped) to produce a so-called frequency modulated continuous wave (FMCW) system.

The radio frequency signal 7060 may be generated by the transmitter 7020 using a local oscillator 7040 coupled with circuitry for applying the pulse gating. In the FMCW case, a voltage-controlled oscillator is used together with a voltage-frequency converter to produce the RF signal 7060 for transmission. The coupling of the transmitted RF signal 7060 to the air may be accomplished using an antenna 7050. The antenna 7050 can be omnidirectional (transmitting power more or less equally in all directions) or directional (transmitting power preferentially in certain directions). It may be advantageous to use a directional antenna 7050 in the apparatus 7000 so that transmitted and reflected energy are primarily coming from one direction. In one implementation of the apparatus 7000, a single antenna 7050 is used for both the transmitter 7020 and the receiver 7030, with a single carrier frequency. Alternatively, multiple receive and transmit antennas 7050 can be used, with multiple carrier frequencies.

The apparatus 7000 is compatible in various embodiments with various types of antenna 7050 such as simple dipole antennas, patch antennas, and helical antennas, and the choice of antenna can be influenced by factors such as the required directionality, size, shape, or cost. It should be noted that the apparatus 7000 can be operated in a manner which has been shown to be safe for human use. The apparatus 7000 has been demonstrated with a total system emitted average power of 1 mW (0 dBm) and lower. The recommended safety level for RF exposure is 1 mW/cm². At a distance of 1 meter from a system transmitting at 0 dBm, the equivalent power density will be at least 100 times less than this recommended limit.

In use, the transmitted RF signal 7060 is reflected off objects that reflect radio waves (such as the air-body interface of the patient 1000), and some of the reflected signal 7070 will be received at a receiver 7030, which can be collocated with the transmitter 7020, or which can be separate from the transmitter 7020, in a so-called "bistatic" configuration. The received signal 7070 and the transmitted signal 7060 can be multiplied together in a mixer 7080 (either in an analog or digital fashion). This mixer 7080 can be of the form of a multiplier (as denoted below in (Eq. 3)) or in a circuit which approximates the effect of a multiplier (e.g., an envelope detector circuit which adds sinusoidal waves). For example, in the CW case, the mixed signal will equal $$m(t)=\gamma\cos(2\pi f_c t)\cos(2\pi f_c t+\phi(t)) \quad \text{(Eq. 3)}$$

where φ(t) is a phase term resulting from the path difference of the transmitted and received signals 7060 and 7070 (in the case where the reflection is dominated by a single reflective object), and γ is the attenuation experienced by the reflected signal 7070. If the reflecting object is fixed, then φ(t) is fixed. In the apparatus 7000, the reflecting object (e.g., the chest of the patient 1000) is in general moving, and φ(t) will be time-varying. As a simple example, if the chest is undergoing a sinusoidal motion of frequency $f_m$ due to respiration, then the mixed signal m(t) contains a component at $f_m$ (as well as a component centred at $2f_c$ which can be simply removed by low pass filtering). The signal at the output of the low pass filter after mixing is referred to as the movement signal or the demodulated sensor movement signal 7003, and contains information about gross bodily (non-respiratory) movement, and respiratory movement.

The amplitude of the demodulated sensor movement signal 7003 is affected by the mean path distance of the reflected signal, leading to detection nulls and peaks in the motion sensor 7010 (i.e. areas where the motion sensor 7010 is less or more sensitive). This effect can be minimised by using quadrature techniques in which the transmitter 7020 simultaneously transmits a signal 90 degrees out of phase (in quadrature) with the signal 7060 of Eq. 1. This results in two reflected signals, both of which can be mixed and lowpass filtered by the mixer 7080, leading to two demodulated sensor signals, referred to as the "I signal" and the "Q signal" in respective I- and Q-"channels". The movement signal 7003 may comprise one or both of these signals.

In the UWB implementation, an alternative method of acquiring a movement signal 7003 may be used. The path distance to the most significant air-body interface can be determined by measuring the delay between the transmitted pulse and peak reflected signal. For example, if the pulse width is 1 ns, and the distance from the motion sensor 7010 to the body is 0.5 metres, then the delay before a peak reflection of the pulse arrives at the receiver 7030 will be 1/(3×10⁸) s=3.33 ns. By transmitting large numbers of pulses (e.g., a 1 ns pulse every 1 μs) and assuming that the path distance is changing slowly over a given period, a movement signal 7003 may be computed as the average of the time delays over that period.

In this way, the motion sensor 7010, e.g., a radio-frequency sensor, can estimate the respiratory movement of the chest wall, or more generally the movement of the part of the body of the patient 1000 whom the apparatus 7000 is monitoring.

As mentioned above, the received signal 7070 can include large motion artefacts, e.g. as the result of gross bodily movement. This is due to the fact that the reflected signals from the body can contain more than one reflection path, and lead to complex signals (for example if one hand is moving towards the sensor, and the chest is moving away). The reception of such signals is useful as it can indicate that the upper body is in motion, which is useful in determining sleep state.

In order to improve the quality of the respiratory movement signal, and more general bodily movement signals, the physical volume from which reflected energy is collected by the sensor unit 1200 can be restricted using various methods. For example, the sensor unit 1200 can be made "directionally selective" (that is, it transmits more energy in certain directions), as can the antenna of the receiver 7030. Directional selectivity can be achieved using directional antennas 7050, or multiple RF transmitters 7020. In alternative forms of the present technology, a continuous wave, an FMCW, or a UWB radar is used to obtain similar signals. A technique called "time-domain gating" can be used to only measure reflected signals 7070 which arise from signals at a certain physical distance from the sensor unit 1200. Frequency domain gating (filtering) can be used to ignore motions of the reflected object above a certain frequency.

In implementations of the apparatus 7000 using multiple frequencies (e.g., at 500 MHz and 5 GHz), the lower frequency can be used to determine large motions accurately without phase ambiguity, which can then be subtracted from the higher-frequency sensor signals (which are more suited to measuring small motions). Using such a sensor unit 1200, the apparatus 7000 collects information from the patient 1000, and uses that information to determine respiratory movement, and more general bodily movement information.

The movement signal 7003 may be stored in memory 7002 of the sensor unit 1200, and/or transmitted over a link (e.g., connection 7008) for storage in the external computing device 7005, for each monitoring session. In one implementation, each monitoring session is one night in duration.

The processor 7006 of the sensor unit 1200, or that of the external computing device 7005, may process the stored movement signal(s) 7003 according to a monitoring process such as those described in detail below. The instructions for the described processes may be stored on a computer-readable storage medium, e.g. the memory 7002 of the sensor unit 1200, and interpreted and executed by a processor, e.g. the processor 7006 of the sensor unit 1200.

8.1.2 Alternative Monitoring Apparatus

Figure 1:
Figure 2:
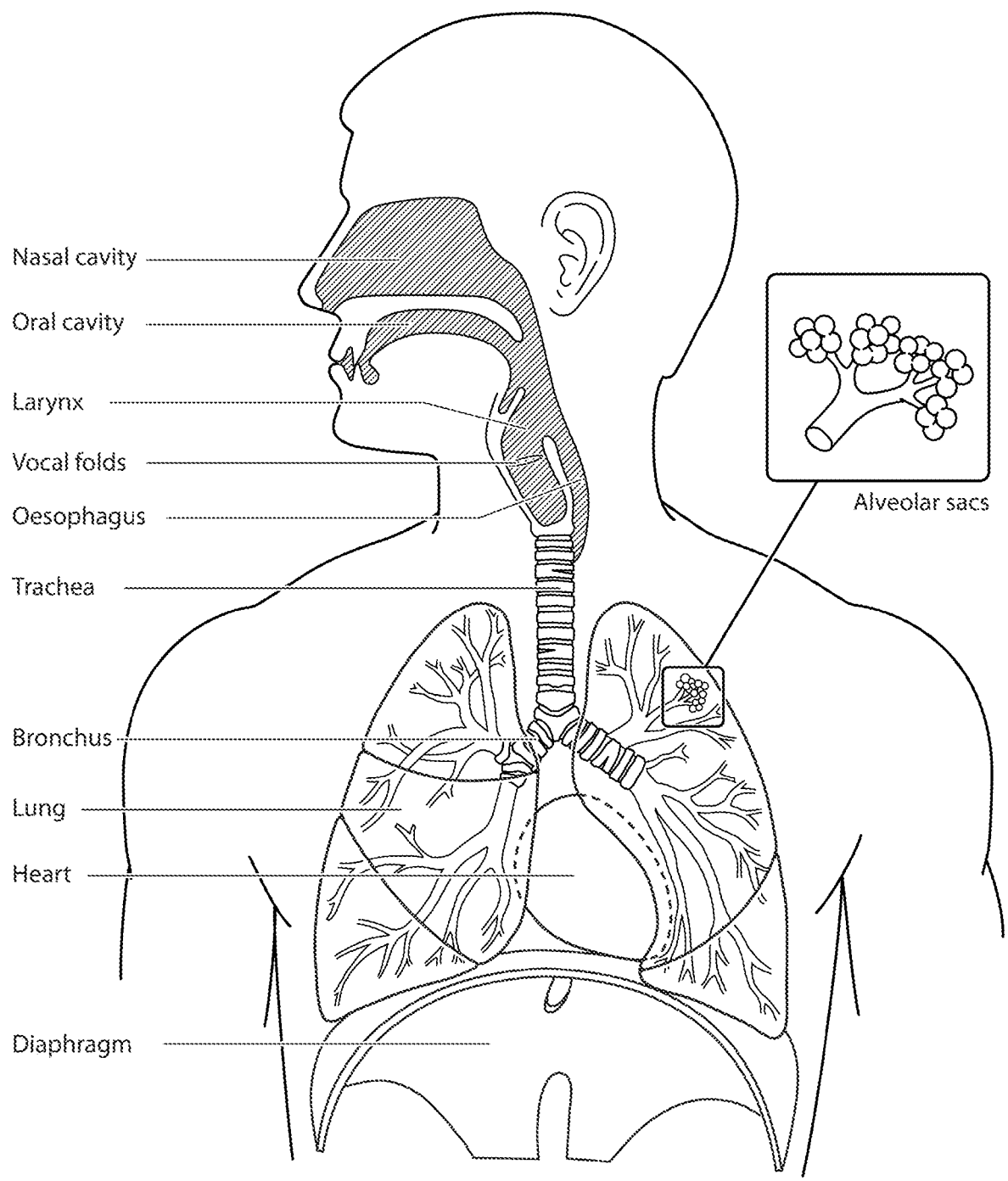
Figure 3:
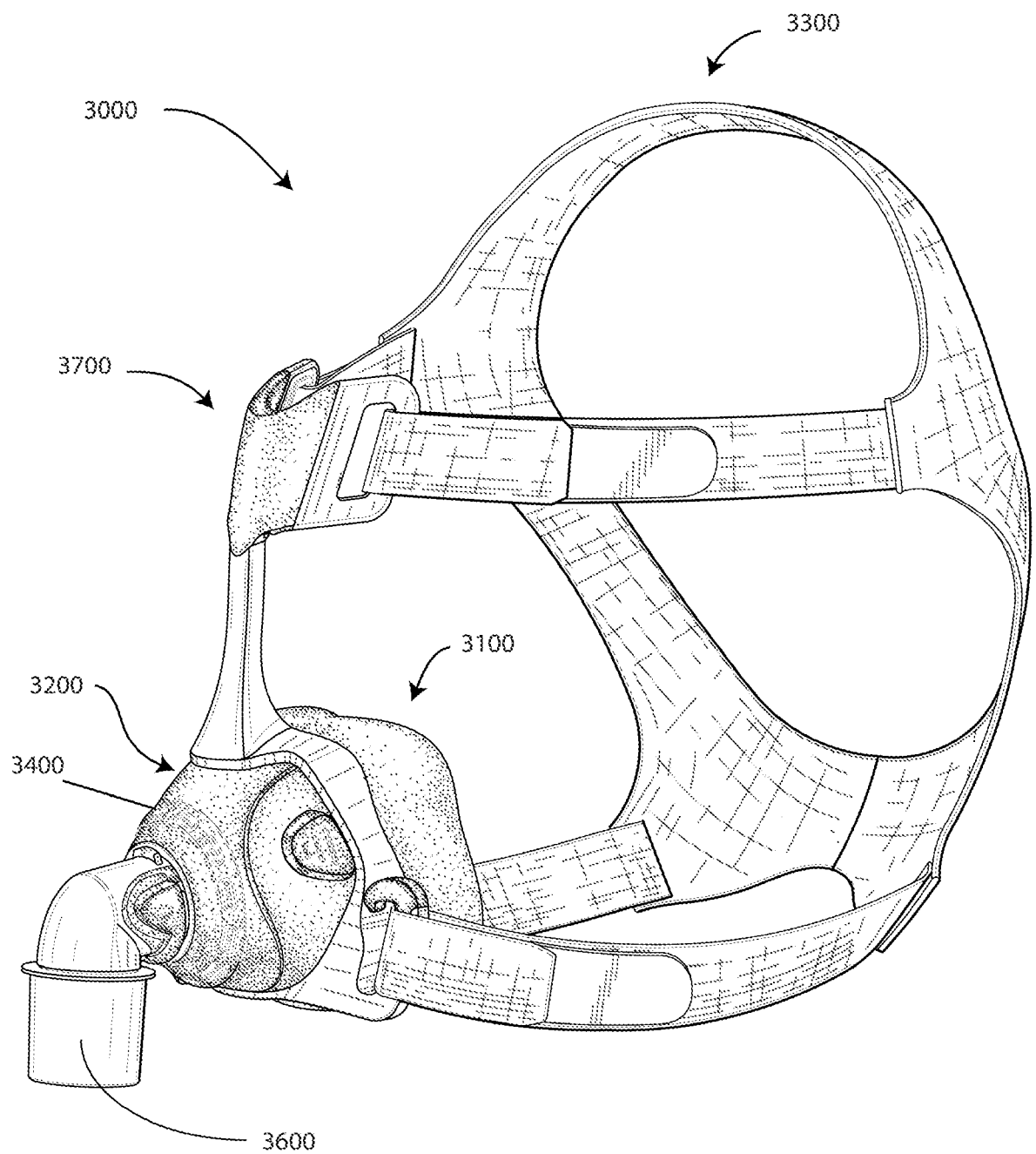

In other forms of the present technology, an RPT device 4000 that is configured to supply respiratory pressure therapy to the patient 1000 via an air circuit 4170 to a patient interface 3000, as illustrated in FIG. 1, may also be configured as a monitoring apparatus.

A patient interface 3000 may comprise the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

An RPT device 4000 may comprise mechanical and pneumatic components 4100, electrical components 4200 and is configured to execute one or more algorithms 4300. The RPT device preferably has an external housing 4010, preferably formed in two parts, an upper portion 4012 and a lower portion 4014. Furthermore, the external housing 4010 may include one or more panel(s) 4015. Preferably the RPT device 4000 comprises a chassis 4016 that supports one or more internal components of the RPT device 4000. The RPT device 4000 may include a handle 4018.

The pneumatic path of the RPT device 4000 preferably comprises one or more air path items, e.g. an inlet air filter 4112, an inlet muffler 4122, a pressure generator 4140 capable of supplying air at positive pressure (preferably a blower 4142), an outlet muffler 4124 and one or more transducers 4270, such as pressure sensors 4272 and flow sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 preferably has an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

In one form of the present technology, the central controller 4230 is one or a plurality of processors suitable to control an RPT device 4000. Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit. In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of the output device 4290, the therapy device controller 4240, the data communication interface 4280, and the humidifier 5000.

In some forms of the present technology, the central controller 4230 is configured to implement the one or more processes described herein expressed as computer programs stored in a non-transitory computer readable storage medium, such as memory 4260.

Data communication interface 4280 may be connectable to a remote external communication network 4282 and/or a local external communication network 4284. The remote external communication network 4282 may be connectable to a remote external device 4286. The local external communication network 4284 may be connectable to a local external device 4288. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol. The local external device 4288 may be a personal computer, mobile phone, tablet or remote control.

In one form, remote external communication network 4282 is the Internet. In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

An output device 4290 may take the form of one or more of a visual, audio and haptic unit. A visual display may be a Liquid Crystal Display (LCD) or Light Emitting Diode (LED) display. A display driver 4292 receives as an input the characters, symbols, or images intended for display on the display 4294, and converts them to commands that cause the display 4294 to display those characters, symbols, or images. A display 4294 is configured to visually display characters, symbols, or images in response to commands received from the display driver 4292.

8.1.3 Monitoring Process

In one aspect of the present technology, a monitoring apparatus carries out a monitoring process to monitor the patient's cardio-pulmonary health from a respiratory signal that is indicative of the respiration of the patient 1000.

In the form of the present technology in which the monitoring apparatus is the unobtrusive apparatus 7000 illustrated in FIG. 7B and the respiratory signal is the respiratory movement signal derived from the movement signal 7003, the monitoring process may be carried out by the processor 7006 of the contactless sensor unit 1200, configured by instructions stored on computer-readable storage medium such as the memory 7002. Alternatively, a processor of the external computing device 7005 may implement all or part of the described monitoring process, having obtained the required data, either raw or partly processed, from the sensor unit 1200 and any other sensors in the apparatus 7000 via the connection 7008 as described above. In such implementations, the above descriptions of the visual display 7015 and the audio output 7017 of the monitoring apparatus 7000 apply equally to comparable elements of the external computing device 7005. In one example, the external computing device 7005 is a clinician-accessible device such as a multi-patient monitoring device that allows a clinician to review data from multiple remote patient data recording devices such as the monitoring apparatus 7000. In these systems, a database may be provided to record patient monitoring data. Through such an external computing device 7005, clinicians may receive a report or alert that a particular patient may require closer observation or should be brought to hospital.

In the form of the present technology in which the monitoring apparatus is the RPT device 4000 and the respiratory signal is a signal representing the respiratory flow rate Qr of the patient 1000 that is derived from one or more of the transducers 4270, the monitoring process may be carried out by the central controller 4230 of the RPT device 4000 configured by instructions stored on computer-readable storage medium such as the memory 4260. Alternatively, the local or remote external device 4288 or 4286 may implement all or part of the described processing, having obtained the required data, either raw or partly processed, from RPT device 4000 via the data communication interface 4280 as described above. In such implementations, the output functions of the output device 4290 of the RPT device 4000 are carried out by comparable elements of the local or remote external device 4288 or 4286.

FIG. 7C is a flow chart illustrating a method 7100 that may be used to implement the monitoring process according to one form of the present technology. The method 7100 may be carried out at the end of each monitoring session on the stored respiratory signal corresponding to that session.

The method 7100 starts at step 7110, at which the respiratory signal is pre-processed. The pre-processing step 7110 (shown dashed in FIG. 7C) is optional and may be omitted from the method 7100. At the next step 7120, the (possibly pre-processed) respiratory signal is analysed to extract one or more respiratory features. The extracted respiratory features may be stored in a memory, for example the memory 7002 of the sensor unit 1200 or that of the external computing device 7005.

The method 7100 then at step 7130 uses the extracted respiratory feature(s) from the just-completed monitoring session, and possibly respiratory features from one or more previous monitoring sessions, to compute a stability measure. The so-created stability measure, or a history of consecutively computed stability measures on a session-by-session basis, may be stored in one or more memories, for example the memory 7002 of the sensor unit 1200 or that of the external computing device 7005 or other memory associated with a processor that computes the stability measure. The stability measure computed at step 7130 may act as a predictor of potential clinical events, in that a change (e.g., rise) in the stability measure may indicate a deterioration in the patient's condition that may be a precursor to a clinical event. The stability measure also changes (e.g., increases) when the patient's condition improves, which is also an event of interest in monitoring a chronic disease.

The stability measure is then evaluated at step 7140 to determine whether it meets a criterion, such as by comparison with one or more thresholds. For example, the stability measure may be compared with a threshold at step 7140, such as in a processor. If the stability measure exceeds the threshold, for example ("Y"), a change point is detected, and step 7150 may generate an alert. If not ("N"), the method 7100 concludes at step 7160. The choice of the threshold affects the sensitivity and specificity of the monitoring process in detecting potential clinical events, and is chosen based on desired levels of sensitivity and specificity when the monitoring process is executed on training data. In some implementations, the threshold may be adjusted between monitoring sessions based on observed false positive and false negative detections. Other evaluations at step 7140 may determine whether the stability measure resides in a particular range, such by a comparison with one or more thresholds attributable to one or more ranges. Accordingly, the automated monitoring process effectively converts, through processing, respiratory signal data, which might appear to be innocuous, into a tool for patient monitoring, i.e., the stability measure, improving not only the monitoring apparatus but also the ability of clinicians in the field to more effectively monitor their patients, such as for making timely and necessary changes in treatment.

In the form of the present technology in which the monitoring apparatus is the unobtrusive monitoring apparatus 7000, the contactless motion sensor 7010 is a Doppler RF motion sensor. As mentioned above, in such an implementation, the movement signal 7003 may comprise two signals, labelled I and Q signals, each generally indicative of bodily movement, but generally 90 degrees out of phase with each other.

Several approaches are possible when the movement signal 7003 comprises I and Q signals. In a "parallel" approach, the steps 7110 and 7120 are performed on each of the I and Q signals in parallel, and the separately obtained features are combined at the end of the feature extraction step 7120. In one implementation of the parallel approach, the pre-processing step 7110 is omitted. In a "combined" approach, the I and Q signals are combined as part of the pre-processing step 7110, and the processing steps 7120 to 7130 are carried out on the combined movement signal. The combined approach has the advantage of less computational complexity than the parallel approach, at the potential cost of lower accuracy.

Alternatively, the contactless motion sensor 7010 may provide a single movement signal 7003. This is handled by an approach referred to as the "single-channel" approach.

The following sections describe implementations of the steps of the monitoring method 7100 of FIG. 7C in more detail.

Figure 4A:
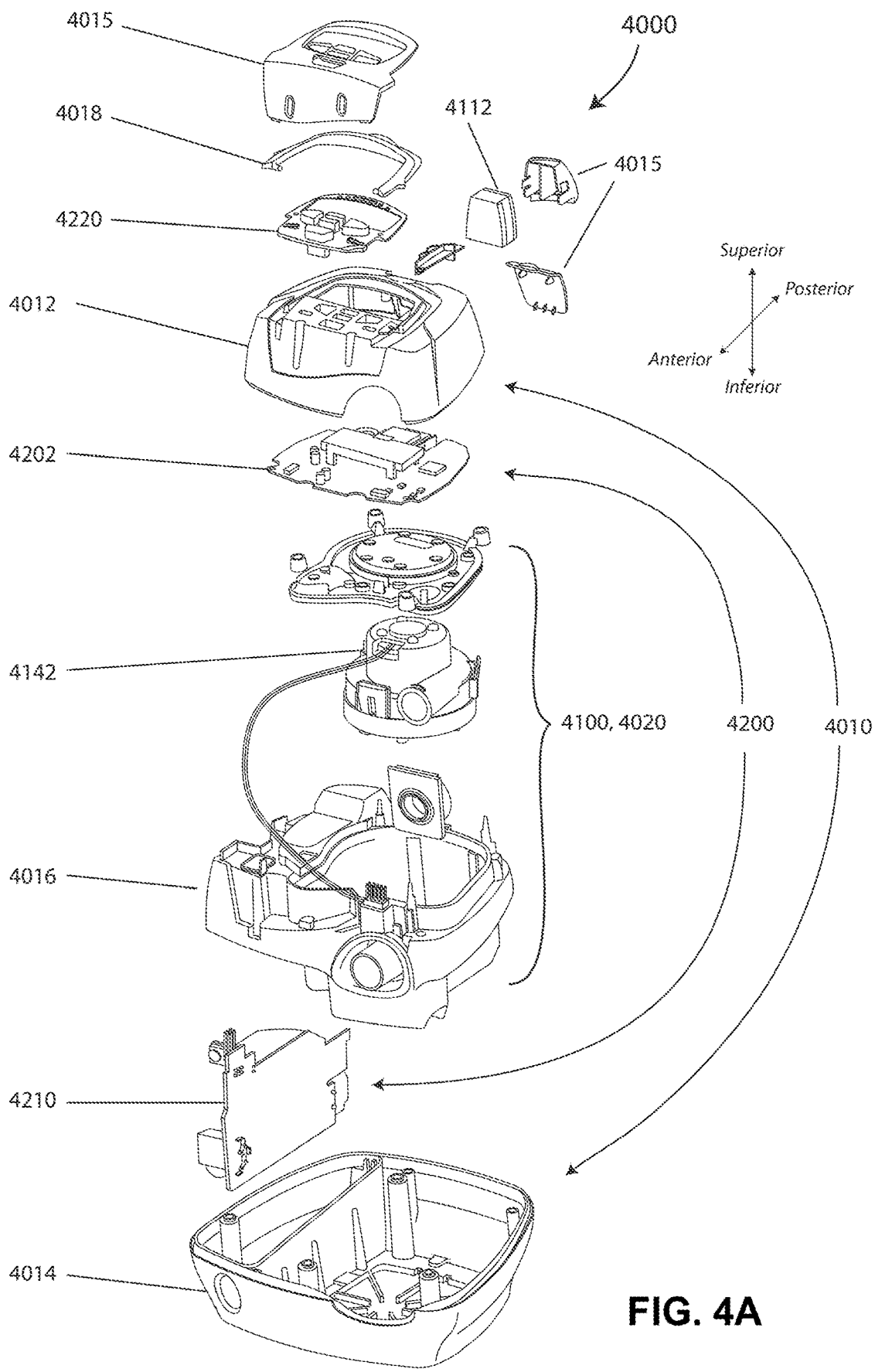
FIG. 4A shows an RPT device in accordance with one form of the present technology.
Figure 4B:
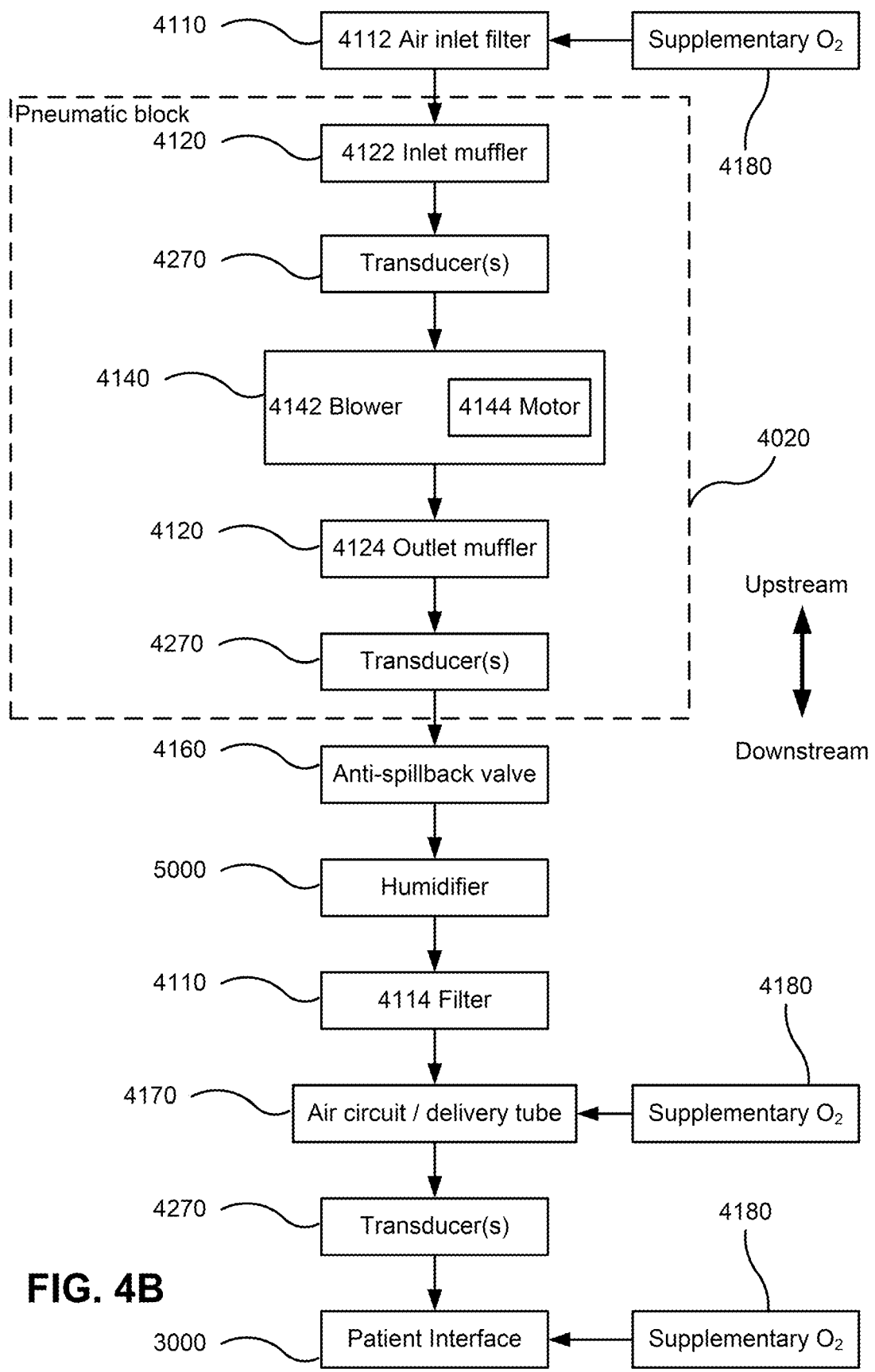
FIG. 4B shows a schematic diagram of the pneumatic path of the RPT device of FIG. 4A in accordance with one form of the present technology. The directions of upstream and downstream are indicated.
Figure 4C:
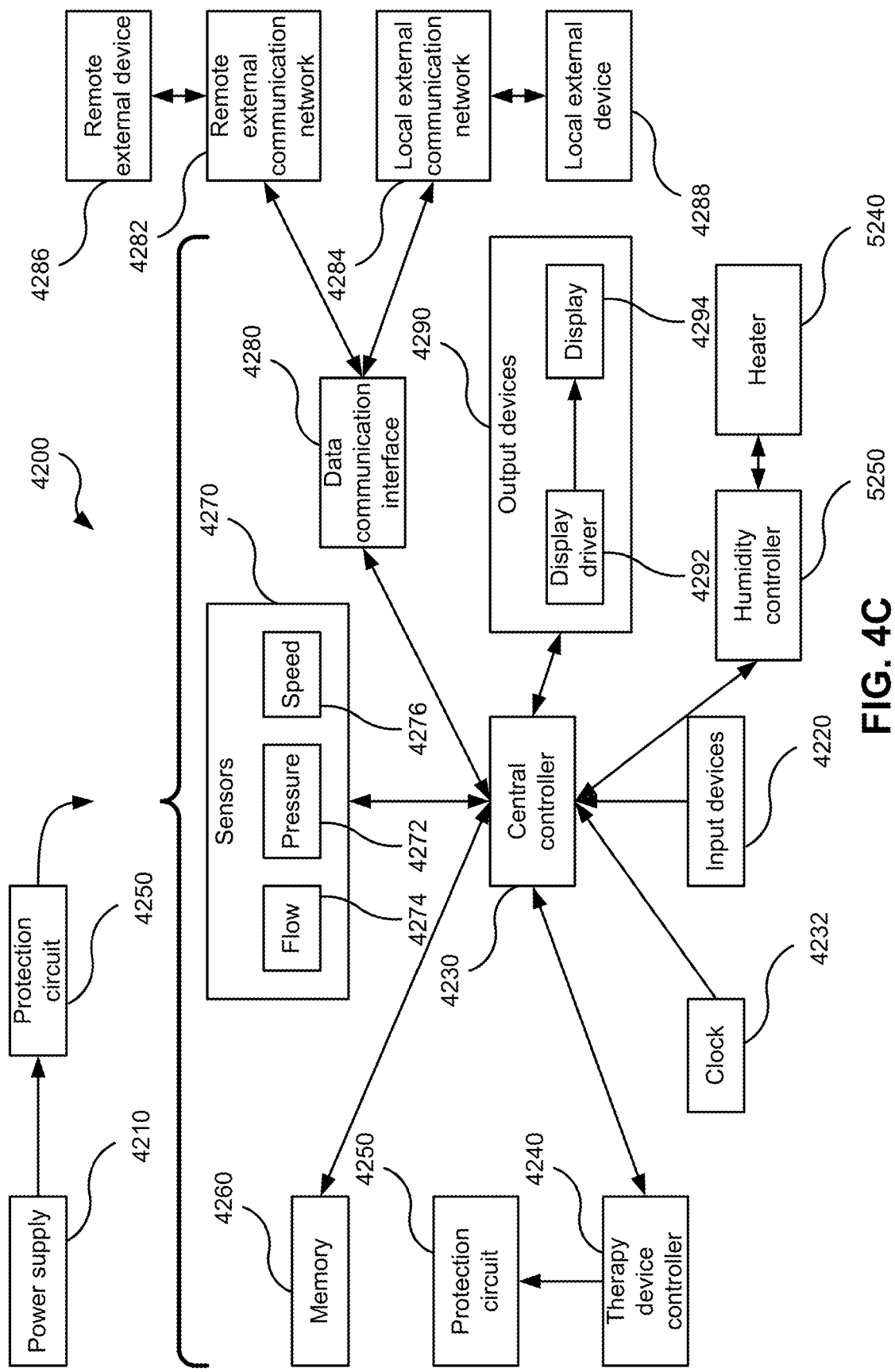
FIG. 4C shows a schematic diagram of the electrical components of the RPT device of FIG. 4A in accordance with one aspect of the present technology.

The implementations of steps 7110 and 7120 are described in terms of the form of the present technology in which the monitoring apparatus is the monitoring apparatus 7000 of FIG. 7B. For the form of the present technology in which the monitoring apparatus is the RPT device 4000 of FIG. 4A, the pre-processing step 7110 may be omitted, and the respiratory feature extraction step 7120 may be performed in conventional fashion on the respiratory flow signal Qr.

The described implementations of steps 7130 to 7150 are generic to both of the above forms of the present technology.

8.1.3.1 Pre-Processing

Under the combined approach, the pre-processing step 7110 begins by combining the I and Q signals in an adaptive geometrical manner into a combined movement signal c. In one implementation, the combination sub-step comprises three stages, applied to a window that slides along the I and Q signals (e.g., progressively processes an amount of data (window size) of the signals over time). In one implementation, the window is of 10 seconds duration with 50% overlap.

a. Check if the signals are 180 degrees out of phase using a cross-correlation, and flip them back to the same quadrant if so.

b. As the vectors (I, Q) form a cloud of points around a quasi-circular arc, subtract the mean of the cloud to centre the arc at (0, 0), locate the minimum $m_{IQ}$ of the centred cloud of points in both directions, and compute the length m of each vector (I, Q) referred to $m_{IQ}$.

$$m_{IQ}=(m_I,m_Q)=(\min[I-\langle I\rangle],\min[Q-\langle Q\rangle]) \quad \text{(Eq. 4)}$$

$$m=\sqrt{(I-m_I)^2+(Q-m_Q)^2} \quad \text{(Eq. 5)}$$

c. Subtract the mean of m to produce the (one dimensional) combined signal c.

$$c=m-\langle m\rangle \quad \text{(Eq. 6)}$$

The combined movement signal c is then (optionally) de-trended to remove baseline wandering. In one implementation, de-trending is implemented using a third-order polynomial:

$$c_1=DT_{poly,3}[c] \quad \text{(Eq. 7)}$$

In another implementation, de-trending is implemented using double-pass median filtering.

The de-trended signal $c_1$ is (optionally) bandpass filtered with a Butterworth bandpass filter with range set to the frequency range of respiratory functioning, this being in one implementation [0.1 Hz, 0.8 Hz] (corresponding to 6 to 48 breaths per minute).

A further (optional) sub-step in the pre-processing step 7110 is noise reduction. In one implementation, particularly suited to signals from Doppler RF motion sensors 7010, which are non-stationary, the noise reduction sub-step is carried out in the wavelet transform domain on the (bandpass filtered) de-trended combined movement signal $c_2$:

$$c_3=W^{-1}MWc_2 \quad \text{(Eq. 8)}$$

where W represents a wavelet transform, for example the 30-coefficient "symmlet" wavelet up to the fifth dyadic level, and M is a masking matrix that passes certain wavelet coefficients and rejects others considered as "perturbative".

The steps to implement the action of M are as follows:

a. Select the dyadic scales for which the "artefactness" (see below) of the wavelet coefficients is above a first threshold $T_A$;

b. From this set of scales, perform a hard thresholding (with threshold $T_C$) of the wavelet coefficients based on the standard deviation.

The "artefactness" at a scale quantifies the degree to which an artefact affects the signal at that scale. Artefactness is a measure of the skewness of the signal which can contain unlikely high amplitude values. The artefactness of a signal x may be computed as:

$$\text{Art}(x) = \frac{2\sigma_x}{\max(|x|) - \min(|x|)} \quad \text{(Eq. 9)}$$

where $\sigma_x$ is the standard deviation of the signal x. The further Art(x) is from 1, the larger the artefact is.

Under the parallel approach, the combination sub-step is omitted from the pre-processing step 7110, and any or all of the subsequent sub-steps (de-trending, filtering, and noise reduction) are performed in parallel on each of the I and Q signals.

Under the single-channel approach, any or all of the de-trending, filtering, and noise reduction sub-steps are performed on the movement signal 7003.

In the description below, the input(s) to the feature extraction step 7120 is /are referred to as (pre-processed) movement signal(s) to reflect the optional nature of the pre-processing step 7110.

8.1.3.2 Respiratory Feature Extraction

FIG. 7D is a block diagram illustrating a method 7200 that may be used to implement the feature extraction step 7120 in the method of FIG. 7C in one form of the present technology.

In the method 7200, an activity estimation and movement detection module 7210 generates an activity count signal and a movement flag series from the (pre-processed) movement signal. (Under the combined or single-channel approach, there is only one (pre-processed) movement signal.) A presence/absence detection module 7220 generates a presence/absence flag series from the (pre-processed) movement signal and the movement flag series. A sleep/wake analysis module 7230 calculates a hypnogram from the presence/absence flag series, the movement flag series, and the activity count signal. A breathing rate estimation module 7240 generates a series of estimates of the breathing rate of the patient from the (pre-processed) movement signal and the hypnogram. A signal selection module 7250 selects sections of the (pre-processed) movement signal, using the movement flag series and the hypnogram.

A modulation cycle metrics calculation module 7255 generates an estimate of the modulation cycle length of the patient's respiration from the selected sections of the (pre-processed) movement signal. An envelope generation module 7260 generates envelopes of the selected sections of the (pre-processed) movement signal using the estimated breathing rate. An SDB event detection module 7265 generates candidate SDB events from the selected sections of the (pre-processed) movement signal using the estimated modulation cycle length. An SDB event confirmation module 7270 confirms the candidate SDB events generated by the SDB event detection module 7265 using the estimated modulation cycle length. Finally, a feature calculation module 7280 calculates respiratory feature values from the confirmed SDB events.

Under the parallel approach, the modules 7210 to 7270 of the method 7200 are simply duplicated to process the two (pre-processed) movement signals 7003 independently. A modified version of the feature calculation module 7280 combines the SDB events from the two parallel processing streams to calculating a single respiratory feature set for the two (pre-processed) movement signals.

The modules 7210 to 7280 of the method 7200 are described in detail in the co-pending PCT application no. PCT/AU2013/000564, published as WO 2013/177621, titled "Method and Apparatus for Monitoring Cardio-Pulmonary Health", by ResMed Sensor Technologies Limited, the entire content of which is herein incorporated by reference.

In one implementation, the feature extraction step 7120 extracts four respiratory features for each monitoring session:

The total number of SDB events;
The $50^{th}$ percentile (median) of the breathing rate;
The $75^{th}$ percentile of the breathing rate; and
The $75^{th}$ percentile of the duration of CSR cycles.

8.1.3.3 Computation of a Stability Measure

Clinical event prediction from respiratory features is an example of a highly imbalanced dataset with very small number of events within a large number of stable sessions, so a robust approach is needed to minimize the number of false positive predictions. The assumption underlying the present technology is that when the patient is stable, the respiratory feature follows one statistical distribution and, at some point before a clinical event, passes through a "change point" to follow a different distribution. The stability measure is therefore computed such that a change of distribution at monitoring session indexed by t results in a rise in the stability measure at or near the monitoring session indexed by t. In other words, the stability measure for a session is an indication of a change point having occurred in the distribution of the respiratory feature at that session. Step 7130 according to the present technology is therefore distribution-based in nature. The distribution-based approach to stability measure computation results in low false positives (high specificity) compared to classification-based approaches.

Two approaches to computing a stability measure at step 7130 are described below. An on-line or sequential approach can, in principle, detect a change point in the distribution of the respiratory feature as soon as it occurs. That is, sufficient data is available after monitoring session t is complete to compute the stability measure at the monitoring session t. The on-line approach is most suitable for ameliorating or preventing clinical events with rapid onset, i.e. a delay of the order of one week between the change point in the distribution and the occurrence of the clinical event.

A retrospective approach can detect a change point in the distribution of the respiratory feature with a delay of the order of one to two weeks, depending on the parameters chosen. The retrospective approach is most suitable for ameliorating or preventing clinical events with more gradual onset, i.e. a delay of the order of two to three weeks between the change point in the distribution and the occurrence of the clinical event.

Each approach forms and analyses a time series $\{y(t)\}$ or $\{y_t\}$ of successive values or samples y of one of the extracted respiratory features indexed by the (integer) monitoring session numbers t. The (integer) monitoring session index t is sometimes shortened in what follows to "time t", in which case it will be understood that time is measured in units of monitoring sessions.

8.1.3.3.1 On-Line or Sequential Approach

The on-line approach is based on Bayesian on-line change point detection (BOPCD). The on-line approach involves a quantity called the run length r at time t, written as $r_t$, which is defined as the number of samples $y_t$ since the last change point of the input sample distribution. Step 7130 under the on-line approach computes the posterior distribution of the run length $r_t$ at time t given all the samples $y_t$ up to and including time t. These samples are written in shorthand form as $y_{1:t}$, so the posterior run length distribution to be computed is written as $p(r_t|y_{1:t})$. The samples $y_{t-r_t+1:t}$ belonging to the current run are written in shortened form as $y_t^{(r)}$.

The posterior run length distribution $p(r_t|y_{1:t})$ may be computed by normalising the joint likelihood $p(r_t, y_{1:t})$ over run length $r_t$:

$$p(r_t \mid y_{1:t}) = \frac{p(r_t, y_{1:t})}{\sum_{r_t} p(r_t, y_{1:t})} \quad \text{(Eq. 10)}$$

The joint likelihood $p(r_t, y_{1:t})$, shortened to $\gamma_t$, may be computed from its previous value $\gamma_{t-1}$ by writing $\gamma_t$ as $p(r_t, r_{t-1}, y_{1:t})$, which may be expanded as a marginalisation over $r_{t-1}$:

$$\begin{aligned}\gamma_t &= p(r_t, r_{t-1}, y_{1:t}) \quad \text{(Eq. 11)}\\ &= \sum_{r_{t-1}} p(r_t, y_t \mid r_{t-1}, y_{1:t-1}) p(r_{t-1}, y_{1:t-1})\\ &= \sum_{r_{t-1}} p(r_t \mid r_{t-1}) p(y_t \mid r_{t-1}, y_{1:t-1}) \gamma_{t-1}\end{aligned}$$

The first factor $p(r_t|r_{t-1})$ in the summed term of Eq. 11 is the conditional prior on the run length, also referred to as the change point prior. In one implementation, the change point prior $p(r_t|r_{t-1})$ has only two non-zero values:

$$p(r_t|r_{t-1}) = \begin{cases} H(r_{t-1}+1), & r_t = 0 \\ 1 - H(r_{t-1}+1), & r_t = r_{t-1}+1 \\ 0, & \text{otherwise} \end{cases} \quad \text{(Eq. 12)}$$

The first non-zero value (for $r_t=0$) is the probability $H(r_{t-1}+1)$ of a change point occurring after a run of length $r_{t-1}$, and the other non-zero value (for $r_t=r_{t-1}+1$) is its complement, the probability of $r_t$ being one greater than $r_{t-1}$, i.e. for the current run to grow by one session. The function $H(r_{t-1}+1)$ is termed the "hazard function". In one implementation, the hazard function $H(r_{t-1}+1)$ may be set to a predetermined constant value h (known as the "hazard rate") that is independent of $r_{t-1}$ (a so-called "memoryless" process) giving rise to a geometric distribution of run lengths with timescale 1/h. In one implementation, the hazard rate h is set to 1/90, that is, one change point per a timescale of 90 monitoring sessions.

The second factor $p(y_t|r_{t-1},y_{1:t-1})$ in the summed term of Eq. 11 is known as the posterior predictive probability, since it is the probability of observing the current sample $y_t$ given all the previous samples $y_{1:t-1}$ and the previous run length $r_{t-1}$. The posterior predictive probability $p(y_t|r_{t-1},y_{1:t-1})$ may be abbreviated to $p(y_t|y_{t-1}^{(r)})$ since it depends only on the previous samples $y_{t-1}^{(r)}$ belonging to the current run.

The Underlying Predictive Model (UPM) is a model of the time series $\{y_t\}$ that is used to compute the posterior predictive probability $p(y_t|y_{t-1}^{(r)})$. In one implementation of the on-line approach, the UPM is based on independent and identically distributed Gaussian samples:

$$y_t \sim N(\mu,\sigma^2) \quad \text{(Eq. 13)}$$

with mean $\mu$ and variance $\sigma^2$ that change at every change point. In one implementation, the mean and variance $\mu$ and $\sigma^2$ are drawn from normal and inverse-Gamma distributions respectively:

$$\mu \sim N\left(\mu_0, \frac{\sigma^2}{k}\right) \quad \text{(Eq. 14)}$$

$$\sigma^{-2} \sim \Gamma(\alpha, \beta)$$

For this reason such a UPM is referred to as a normal-inverse-Gamma (NIG) model. The parameters $\mu_0$, $\kappa_0$, $\alpha_0$, and $\beta_0$ of the (NIG) model are determined by fitting a normal-inverse-Gamma model to a training data set.

To compute the posterior predictive probability at time t, the parameters of the UPM are first updated for all times from 1 to the current time t:

$$\mu_{1:t} = \left[\mu_0 \quad \frac{\kappa_{1:t-1}\mu_{1:t-1} + y_t}{\kappa_{1:t-1}+1}\right] \quad \text{(Eq. 15)}$$

$$\kappa_{1:t} = [\kappa_0 \quad 1+\kappa_{1:t-1}]$$

$$\alpha_{1:t} = [\alpha_0 \quad \alpha_{1:t-1}+0.5]$$

$$\beta_{1:t} = \left[\beta_0 \quad \beta_{1:t-1} + \frac{\kappa_{1:t-1}(y_t-\mu_{1:t-1})^2}{2(\kappa_{1:t-1}+1)}\right]$$

The variance $\sigma^2$ of the NIG model is then computed as $$\sigma^2 = \frac{\beta_t(\kappa_t+1)}{\alpha_t+\kappa_t} \quad \text{(Eq. 16)}$$

Finally, the posterior predictive probability $p(y_t|y_{t-1}^{(r)})$ is computed as $$p(y_t|y_{t-1}^{(r)}) = \frac{\Gamma(\alpha_t+0.5)}{\Gamma(\alpha_t)} \frac{1}{\sqrt{2\alpha_t\pi\sigma^2}} \left[1 + \frac{1}{2\alpha_t\sigma^2}(y_t-\mu_t)^2\right]^{-(\alpha_t+0.5)} \quad \text{(Eq. 17)}$$

As an aside, the posterior run length distribution $p(r_t|y_{1:t})$ at time t may be used to compute the marginal predictive distribution $p(y_{t+1}|y_{1:t})$ of the next sample $y_{t+1}$, given all the samples $y_{1:t}$. The marginal predictive distribution $p(y_{t+1}|y_{1:t})$ may be computed in a way that preserves uncertainty in the run length $r_t$ by marginalisation of the posterior predictive probability $p(y_{t+1}|y_t^{(r)})$ over the run length $r_t$:

$$p(y_{t+1}|y_{1:t}) = \sum_{r_t} p(y_{t+1}|y_t^{(r)})p(r_t|y_{1:t}) \quad \text{(Eq. 18)}$$

The posterior predictive probability $p(y_{t+1}|y_t^{(r)})$ for each value of run length $r_t$ may be computed from the UPM as described above.

The stability measure $S_t$ under the on-line approach may be computed as the probability at time t of a change point having occurred since the last change point was detected. This probability is computed as the sum of the values of the posterior run length distribution $p(r_t|y_{1:t})$ over all possible run lengths since the previous change point was detected. That is, the sum is computed over all values of run length $r_t$ from zero up to the current time t less the time of the previous change point:

$$S_t = \sum_{r_t=0}^{t-t_0} p(r_t|y_{1:t}) \quad \text{(Eq. 19)}$$

where the previous change point before time t was detected at time $t_0$. (The previous alert time $t_0$ is initialised to zero before any change points are detected.)

In one form of the present technology, as described below, a clinician is able to issue manual alerts to the monitoring apparatus 7000 through the user interface of their associated external computing device 7005 based on the clinician's inspection of the respiratory features being received at, or computed by, the external computing device 7005. If such a manual alert is issued, the value of the previous alert time $t_0$ is updated to the time at which the manual alert was issued.

FIG. 7E contains a flow chart illustrating a method 7300 that may be used to implement the stability measure computation step 7130 of the method 7100 of FIG. 7C under the on-line approach according to one form of the present technology. The method 7300 is carried out iteratively, one iteration after each monitoring session.

The method 7300 starts at step 7310, where the joint likelihood $p(r_t, y_{1:t})$ (i.e. $\gamma_t$) is initialised (i.e. assigned a value for t=0), to 1 in one implementation. The step 7310 is only carried out at the first iteration of the method 7300, and hence is shown dashed in FIG. 7E. At step 7320, the current time t is incremented and the current sample $y_t$ is received. Step 7330 follows, at which the method 7300 computes the current posterior predictive probability $p(y_t|y_{t-1}^{(r)})$ using the UPM and the current sample $y_t$ using Eqs. 15 to 17. Step 7340 then computes the current joint likelihood $p(r_t, y_{1:t})=\gamma_t$ from the previous joint likelihood $\gamma_{t-1}$ and the current posterior predictive probability $p(y_t|y_{t-1}^{(r)})$ using Eq. 11. For run length $r_t$ equal to zero, there are t terms in the sum of Eq. 11. However, for values of run length $r_t$ that are greater than zero, there is only one term in the sum of Eq. 11, as there is only one value of $r_{t-1}$ at which the change point prior (Eq. 12) is non-zero, namely $r_{t-1}=r_t-1$. This fact gives the on-line approach its computational efficiency.

At the next step 7350, the method 7300 computes the current posterior run length distribution $p(r_t|y_{1:t})$ by normalising the current joint likelihood $p(r_t, y_{1:t})$ as in Eq. 10. Step 7360 then computes the current stability measure $S_t$ from the current posterior run length distribution $p(r_t|y_{1:t})$ using Eq. 19. The method 7300 then concludes.

8.1.3.3.2 Retrospective Approach

The retrospective approach to step 7130 works by comparing the probability distributions of sub-sequences of the time series $\{y(t)\}$ before and after a certain time. Step 7130 under the retrospective approach computes the stability measure at that time as the dissimilarity between the two distributions.

Notationally, a sub-sequence Y(t) of length k of the time series {y(t)} is defined as $$Y(t) \triangleq [y(t) \ldots y(t+k-1)] \quad \text{(Eq. 20)}$$

where k is a parameter of the retrospective approach. Each sub-sequence Y(t) is treated as a k-component vector that is a sample from an underlying k-dimensional joint distribution. A set Ψ(t) of n consecutive sub-sequences Y(t) at time t is defined as $$\psi(t) \triangleq \{Y(t), Y(t+1), Y(t+2), \ldots Y(t+n-1)\} \quad \text{(Eq. 21)}$$

where n is a further parameter of the retrospective approach. The probability distribution of the set Ψ(t) of n sub-sequences Y(t) is written as $P_t$.

The retrospective approach computes a symmetrical dissimilarity $D_s$ between the distribution $P_t$ and the distribution $P_{t+n}$ of the set Ψ(t+n) of n sub-sequences, n samples later than the set Ψ(t). In one implementation, the symmetrical dissimilarity $D_s$ makes use of a measure of dissimilarity $D_f(P\|P')$ between two distributions P and P' known as the f-divergence, and defined as $$D_f(P\|P') \triangleq \int p'(Y) f\left(\frac{p(Y)}{p'(Y)}\right) dY \quad \text{(Eq. 22)}$$

where f is a convex function such that f(1)=0, and p(Y) and p'(Y) are the probability density functions (densities) of the distributions P and P' respectively. The symmetrical dissimilarity $D_s$ may be computed as the sum of the f-divergence $D_f(P_t\|P_{t+n})$ between the distribution $P_t$ and the distribution $P_{t+n}$, and the f-divergence $D_f(P_{t+n}\|P_t)$ between the distribution $P_{t+n}$ and the distribution $P_t$:

$$D_s(P_t\|P_{t+n}) = D_f(P_t\|P_{t+n}) + D_f(P_{t+n}\|P_t) \quad \text{(Eq. 23)}$$

The symmetrical dissimilarity $D_s$ is so termed because the symmetrical dissimilarity $D_s$ between $P_t$ and $P_{t+n}$ is the same as the symmetrical dissimilarity $D_s$ between $P_{t+n}$ and $P_t$. In general, the f-divergence $D_f$ of Eq. 22 is not symmetrical in this sense. The symmetrical dissimilarity $D_s$ computed according to Eq. 23 takes a high value when either the f-divergence $D_f$ between $P_t$ and $P_{t+n}$ or the f-divergence $D_f$ between $P_{t+n}$ and $P_t$ is high. The symmetrical dissimilarity $D_s$ is therefore more sensitive in detecting change points than either the f-divergence $D_f$ between $P_t$ and $P_{t+n}$ alone or the f-divergence $D_f$ between $P_{t+n}$ and $P_t$ alone. The symmetrical dissimilarity $D_s$ between $P_t$ and $P_{t+n}$ may therefore be used as a stability measure $S_{t+n}$ for the patient 1000 at time t+n. A high value of the symmetrical dissimilarity $D_s$ between $P_t$, a probability distribution of a set Ψ(t) comprising sub-sequences Y(t) substantially composed of samples of the time series {y(t)} before the monitoring session t+n, and $P_{t+n}$, a probability distribution of a set Ψ(t+n) comprising sub-sequences Y(t+n) substantially composed of samples of the time series {y(t)} after the monitoring session t+n, indicates that a change point in the time series {y(t)} is likely to be present between monitoring sessions (t+n−1) and (t+n).

To evaluate the stability measure $S_{t+n}$ at the monitoring session t+n using the definition in Eq. 23 requires samples y(t) from times up to and including the time t+2n+k−2. In other words, when sample y(T) is received at time T, the stability measure S according to the retrospective approach may be computed at time T−n−k+2. Therefore, a rise in the stability measure S computed using the most recent sample y(T) at time T according to the retrospective approach indicates that a change point occurred approximately n+k−2 monitoring sessions before the time T. The retrospective approach is therefore said to have a delay of n+k−2 samples.

In one implementation, the convex function f used in the definition of the f-divergence (Eq. 22) is the Kullback-Leibler divergence defined as f(t)=t log(t). In another implementation, the convex function f is the Pearson divergence defined as a quadratic function:

$$f(t) = \frac{1}{2}(t-1)^2 \quad \text{(Eq. 24)}$$

Substituting the Pearson divergence f(t) of Eq. 24 into Eq. 22 gives the Pearson dissimilarity $D_{PE}$.

Since the densities p(Y) and p'(Y) of the distributions $P_t$ and $P_{t+n}$ are unknown, the symmetrical dissimilarity $D_s$ cannot be computed directly. One implementation of the retrospective approach uses conventional methods to estimate the densities p(Y) and p'(Y) from the sets Ψ(t) and Ψ(t+n) respectively, and then applies Eqs. 22 and 23 to compute the symmetrical dissimilarity $D_s$ from the estimated densities. However, conventional density estimation methods tend to be less accurate as the number of dimensions (in this case k) increases.

An alternative implementation of the retrospective approach estimates the ratio between the densities p(Y) and p'(Y). Density ratio estimation is easier than estimation of the separate densities p(Y) and p'(Y) to comparable accuracy.

The density ratio g(Y)=p(Y)/p'(Y) may be approximated by a weighted sum of kernel basis functions:

$$\hat{g}(Y) = \sum_{l=1}^{n} \theta_l K(Y, Y_l) \quad \text{(Eq. 25)}$$

where the kernel basis function K is a Gaussian function:

$$K(Y, Y') = \exp\left(-\frac{1}{2\sigma^2}\|Y - Y'\|^2\right) \quad \text{(Eq. 26)}$$

with a kernel width σ that is determined based on cross-validation, and the weights or coefficients $\theta_l$ are elements of a parameter n-vector θ. The kernel centres $Y_l$ (l=1, ..., n) are the n sub-sequences Y(t), ..., Y(t+n−1) making up the set Ψ(t).

The optimal parameter vector $\hat{\theta}$ of the approximation given in Eq. 25 to the density ratio g(Y) may be found by fitting the approximation $\hat{g}$ to the true density ratio g under squared loss. This is equivalent to minimising the following objective function O over the parameter vector θ:

$$O(\theta) = \frac{1}{2}\theta^T H \theta - h^T \theta + \frac{\lambda}{2}\theta^T \theta \quad \text{(Eq. 27)}$$

where H is an n-by-n matrix with (l, l')-th element H(l, l') given by $$H(l, l') = \frac{1}{n}\sum_{j=1}^{n} K(Y'_j, Y_l) K(Y'_j, Y_{l'}) \quad \text{(Eq. 28)}$$

where the $Y'_j$ (j=1, . . . , n) are the n sub-sequences $Y(t+n), \ldots, Y(t+2n-1)$ making up the set $\Psi(t+n)$. The vector h is an n-vector with l-th element h(l) given by $$h(l) = \frac{1}{n}\sum_{i=1}^{n} K(Y_i, Y_l) \quad \text{(Eq. 29)}$$

The last term in the objective function of Eq. 27 is a penalty term, included for regularisation purposes, with $\lambda$ as the regularisation parameter.

The objective function in Eq. 27 is minimised by the parameter vector $\hat{\theta}$ given by:

$$\hat{\theta} = (H + \lambda I_n)^{-1} h \quad \text{(Eq. 30)}$$

The Pearson dissimilarity $D_{PE}(P_t \| P_{t+n})$ of Eq. 22 may be approximated as $$\hat{D}_{PE}(P_t \| P_{t+n}) = -\frac{1}{2n}\sum_{j=1}^{n}(\hat{g}(Y'_j))^2 + \frac{1}{n}\sum_{i=1}^{n}\hat{g}(Y_i) - \frac{1}{2} \quad \text{(Eq. 31)}$$

The Pearson dissimilarity $D_{PE}(P_{t+n} \| P_t)$ may be approximated in similar fashion to $\hat{D}_{PE}(P_t \| P_{t+n})$ by interchanging the sub-sequences $Y_i$ (i=1, . . . , n) and $Y'_j$ (j=1, . . . , n). The resulting approximation $\hat{D}_{PE}(P_{t+n} \| P_t)$ is then added to the approximation $\hat{D}_{PE}(P_t \| P_{t+n})$ to obtain the symmetrical dissimilarity $D_S(P_t \| P_{t+n})$, which is the stability measure $S_{t+n}$ under the retrospective approach.

FIG. 7F contains a flow chart illustrating a method 7400 that may be used to implement the stability measure computation step 7130 of the method 7100 of FIG. 7C under the retrospective approach according to one form of the present technology.

The method 7400 starts at step 7410, which forms the two sets of sub-sequences $Y_i$ (i=1, . . . , n) and $Y'_j$ (j=1, . . . , n) making up the sets $\Psi(t)$ and $\Psi(t+n)$ respectively according to Eq. 21. Because of the definitions of these sub-sequences, the method 7400 is carried out on or after the time t+2n+k−2. Step 7420 follows, at which the matrix H and the vector h are computed using Eqs. 28 and 29 and the kernel definition Eq. 26. At the next step 7430, Eq. 30 is applied to compute the parameter vector $\hat{\theta}$. Step 7440 follows, at which the method 7400 uses the parameter vector $\hat{\theta}$ to compute the approximation to the Pearson dissimilarity $D_{PE}(P_t \| P_{t+n})$ using Eqs. 31 and 25.

At step 7450, the sub-sequences $Y_i$ (i=1, . . . , n) and $Y'_j$ (j=1, . . . , n) are interchanged. Steps 7460, 7470, and 7480 repeat the processing of steps 7420, 7430, and 7440 on the interchanged sub-sequences $Y'_j$ (j=1, . . . , n) and $Y_i$ (i=1, . . . , n) to obtain an approximation to the Pearson dissimilarity $D_{PE}(P_{t+n} \| P_t)$. Finally, at step 7490 the approximations to $D_{PE}(P_t \| P_{t+n})$ and $D_{PE}(P_{t+n} \| P_t)$ are added together to obtain the symmetrical dissimilarity $D_S(P_t \| P_{t+n})$, which is a stability measure $S_{t+n}$ at the time t+n according to the retrospective approach.

In one implementation of the method 7400, the parameters n and k are 10 and 5 respectively, so the delay of the retrospective approach is n+k−2=13 samples. The kernel width $\sigma$ and the regularisation parameter $\lambda$ are obtained by cross-validation, as the values from two discrete candidate sets that minimise the objective function in Eq. 27 over plural randomly chosen subsets of the sets $\Psi(t)$ and $\Psi(t+n)$ of sub-sequences $Y_i$ and $Y'_j$.

8.1.3.3.3 Combined Approach

The combined approach to step 7130 computes both the on-line stability measure and the retrospective stability measure as described above to generate alerts. In one implementation of the combined approach, the combined approach generates an alert when the on-line stability measure meets a first criterion (e.g., one or more threshold comparisons) and the retrospective stability measure at the same time meets a second criterion (e.g., one or more threshold comparisons). In another implementation of the combined approach, the combined approach generates an alert when either the on-line stability measure meets a first criterion (e.g., one or more threshold comparisons) or the retrospective stability measure at the same time meets a second criterion (e.g., one or more threshold comparisons).

8.1.3.4 Alert Generation

The clinical alert generated at step 7150 may include a warning or alert message taking a number of forms. For example, the processor 7006, to generate a clinical alert to the patient 1000, may activate a status light (e.g., an LED or an icon on the display device 7015) of the monitoring apparatus 7000. A more detailed message concerning the assessment of the indicator may also be displayed to the patient 1000 on the display device 7015. Optionally, the processor 7006 may also, or alternatively, send an alert message via the connection 7008 to the external computing device 7005 associated with a clinician. Such a message may take the form of a wired or wireless communication. For example, the processor 7006 may generate an alert message via a paging system such as by automatically dialing a paging system. The processor 7006 may also be configured to generate an automated voice phone call message. The processor 7006 may also send the alert message by a fax transmission. In some embodiments, the processor 7006 may also send an alert message via any internet messaging protocol, such as an email message, or by any other internet data file transport protocol. The alert messages may even be encrypted to keep patient information confidential. A typical alert message may identify the patient. Such a message may also include data recorded by the monitoring apparatus 7000 or any other recorded patient information. Optionally, in some embodiments, the alert message may even express that the patient should be considered for additional treatment, hospitalization, or an evaluation due to the detection of a potential clinical event.

While alert messages may be directed by the processor 7006 to the patient via the display device 7015 of the monitoring apparatus 7000 and to the clinician via the connection 7008, in some embodiments, the alert messages could be directed more selectively. For example, a first alert message may be only transmitted to a clinician by only transmitting the alert message to an external computing device 7005 through the connection 7008 without showing any alert on the display device 7015. However, a second alert message, which may be a more urgent message, could then be actively displayed on the display device 7015 in addition to being transmitted to the external computing device 7005. An audible alarm from an optional speaker controlled by the processor 7006 may also be implemented. Use of an audible alarm may depend on the urgency of the alert message.

In one form of the present technology, a clinician is able to issue manual alerts to the monitoring apparatus 7000 through the user interface of their associated external computing device 7005 based on the clinician's inspection of the respiratory features being received at the external computing device 7005.

8.1.3.4.1 Queries

In another form of the present technology, the processor 7006 may condition an alert on responses to a patient query that may serve to avoid unnecessary alerts. In a variant of the method 7100, upon the stability measure meeting a criterion (step 7140), rather than immediately generating an alert, as at step 7150, the processor 7006 may prompt the patient 1000 to take an action, such as take their prescribed medication, or trigger a presentation of a query to the patient 1000 to provide a response. The display device 7015 under control of the processor 7006 may present the query to the patient 1000, prompting the patient 1000 to input a response via a user interface. The presented question or questions of the query may be selected from a database, or other data structure of questions, such as a data structure in the memory 7002 of the monitoring apparatus 7000. The processor 7006 may then evaluate the received responses to the query. Based on this evaluation, the processor 7006 may generate an alert as at step 7150, abort an alert, and/or delay generation of an alert pending responses to one or more additional queries. Such additional queries may be triggered after a certain time, after a further detected change point, or after a further use of the monitoring apparatus 7000. In the forms of the present technology in which step 7150 comprises sending an alert message to the external computing device 7005 associated with a clinician, the received query responses may instead be forwarded to the external computing device 7005 for manual evaluation by the clinician. Based on their evaluation, the clinician may decide to maintain or to cancel the alert.

Such queries may serve to reduce false positives (e.g., when the alert results in clinical intervention with the patient and the clinical intervention is later found to have been unnecessary). Some false positives may be due to changes in patient behavior, which may be corrected without clinical intervention. Such behaviors may include missed or incorrect dosage of medication, non-compliance with dietary instructions and/or rest requirements, and the like. The query questions may address pharmaceutical and/or lifestyle compliance by the patient (e.g., has the patient been taking prescribed medication and/or following a physician's treatment advice, etc.). Optionally, in some cases, one or more questions may address the operational integrity of the monitoring apparatus 7000 to ensure that the received respiratory signal is valid. Optionally, the processor 7006 may pursue a series of queries over a predetermined span of time (such as one or more monitoring sessions) and generate an alert only after the predetermined span of time has elapsed.

Under the on-line approach, if the processor 7006 aborts an alert in response to a detected change point, or a generated alert is subsequently manually cancelled by a clinician, the processor 7006 may revert the previous alert time to (used in Eq. 19) to the time of the last-but-one generated alert.

8.2 Example Results

FIG. 8 contains a graph 8000 showing example results obtained from the monitoring apparatus 7000 using the method 7100. The upper trace 8010 shows one of the above-mentioned respiratory features, namely $75^{th}$ percentile of respiratory rate over the session, over 400 sessions indexed by t. The grey band 8015 shows a 28-session interval symmetrically surrounding an ADHF event (indicated by the upward arrow 8020) experienced by the patient at approximately session number 182. The lower trace 8050 shows peaks at the sessions t where the stability measure $S_t$ computed by the retrospective approach exceeded a threshold, and hence step 7150 generated an alert. In particular the double peak 8060 coincides with the ADHF event. Other peaks, e.g. 8070, do not coincide with ADHF events and therefore represent "false positives".

8.3 Glossary

For the purposes of the present technology disclosure, in certain forms of the present technology, one or more of the following definitions may apply. In other forms of the present technology, alternative definitions may apply.

8.3.1 General

Air: In certain forms of the present technology, air may be taken to mean atmospheric air, and in other forms of the present technology air may be taken to mean some other combination of breathable gases, e.g. atmospheric air enriched with oxygen.

Continuous Positive Airway Pressure (CPAP): CPAP treatment will be taken to mean the application of a supply of air to the entrance to the airways at a pressure that is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

8.3.2 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory flow, airflow, patient airflow, respiratory airflow (Qr): These synonymous terms may be understood to refer to the RPT device's estimate of respiratory airflow, as opposed to "true respiratory flow" or "true respiratory airflow", which is the actual respiratory flow experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

8.3.3 RPT Device Parameters

Flow rate (or flow): The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. Total flow, Qt, is the flow rate of air leaving the RPT device. Vent flow, Qv, is the flow rate of air leaving a vent to allow washout of exhaled gases. Leak flow, Ql, is the flow rate of unintentional leak from a patient interface system. Respiratory flow, Qr, is the flow rate of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

8.4 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

8.5 Reference Signs List patient 1000
sensor unit 1200
patient interface 3000
seal-forming structure 3100
plenum chamber 3200
stabilising structure 3300
vent 3400
connection port 3600
forehead support 3700
RPT device 4000
external housing 4010
upper portion 4012
portion 4014
panel 4015
chassis 4016
handle 4018
pneumatic block 4020
pneumatic component 4100
inlet air filter 4112
inlet muffler 4122
outlet muffler 4124
pressure generator 4140
blower 4142
air circuit 4170
electrical component 4200
PCBA 4202
electrical power supply 4210
input device 4220
central controller 4230
therapy device controller 4240
protection circuit 4250
memory 4260
transducer 4270
pressure sensor 4272
flow sensor 4274
data communication interface 4280
remote external communication network 4282
local external communication network 4284
remote external device 4286
local external device 4288
output device 4290
display driver 4292
display 4294
algorithm 4300
humidifier 5000
monitoring apparatus 7000
microcontroller unit 7001
memory 7002
movement signal 7003
communications circuitry 7004
external computing device 7005
processor 7006
connection 7008
motion sensor 7010
display device 7015
audio output 7017
transmitter 7020
receiver 7030
local oscillator 7040
antenna 7050
radio frequency signal 7060
reflected signal 7070
mixer 7080
monitoring method 7100
step 7110
step 7120
step 7130
step 7140
step 7150
step 7160
method 7200
movement detection module 7210
presence/absence detection module 7220
sleep/wake analysis module 7230
breathing rate estimation module 7240
signal selection module 7250
modulation cycle metrics calculation module 7255
envelope generation module 7260
SDB event detection module 7265
SDB event confirmation module 7270
feature calculation module 7280
method 7300
step 7310
step 7320
step 7330
step 7340
step 7350
step 7360
method 7400
step 7410
step 7420
step 7430
step 7440
step 7450
step 7460
step 7470
step 7480
step 7490
graph 8000
trace 8010 grey band 8015
upward arrow 8020
trace 8050
peak 8060

The invention claimed is:

1. A method of monitoring chronic respiratory disease state of a patient in a system comprising a plurality of monitoring devices and a remote server configured for multi-patient monitoring, the plurality of monitoring devices and the remote server being configured for communications over a network, the method comprising:
 extracting, in a processor of the system, for each of a plurality of monitoring sessions, a respiratory feature from a respiratory signal indicative of the patient's respiration during the monitoring session and generated with a monitoring device of the plurality of monitoring devices, the respiratory signal derived from at least one sensor;
 computing, in a processor of the system, a stability measure of the patient for a monitoring session, the stability measure representing an indication of a change point having occurred at the monitoring session in a statistical distribution of the respiratory feature; and
 generating, by a processor of the system, an output comprising an alert or presentation based on the stability measure, wherein the generating comprises transmitting, via communications over the network, a message for the output, and displaying, on a display device, the alert or presentation in response to the transmitting,
 wherein the chronic respiratory disease state of the patient comprises Chronic Obstructive Pulmonary Disease or a cardio-pulmonary disorder,
 wherein the computing forms and analyses a time series of successive values of the extracted respiratory feature indexed by monitoring session identifiers, wherein each monitoring session of the plurality of monitoring sessions is a duration, and wherein the indication is a sum of values of a posterior distribution of run length for the monitoring session given values of the respiratory feature up to and including the monitoring session.

2. The method of claim 1 wherein the stability measure changes (a) to indicate a deterioration in the patient's condition, and (b) to indicate improvement in the patient's condition.

3. The method of claim 2 wherein the duration is a duration of a night.

4. A method according to claim 3, wherein the indication is a probability of a change point having occurred at the monitoring session in the statistical distribution of the respiratory feature.

5. A method according to claim 3, further comprising computing, in a processor of the system, a further stability measure representing an further indication of a change point having occurred at the monitoring session in a statistical distribution of the respiratory feature, wherein the further indication is a measure of dissimilarity of probability distributions of two sets of sub-sequences of a time series formed from the respiratory feature, the two sets comprising sub-sequences substantially composed of samples of the time series before and after the monitoring session respectively.

6. A method according to claim 1, wherein the respiratory feature is a percentile of breathing rate.

7. A method according to claim 1, wherein the respiratory feature is a total number of sleep disordered breathing events.

8. A method of monitoring chronic respiratory disease state of a patient in a system comprising a plurality of monitoring devices and a remote server configured for multi-patient monitoring, the plurality of monitoring devices and the remote server being configured for communications over a network, the method comprising:
 extracting, in a processor of the system, for each of a plurality of monitoring sessions, a respiratory feature from a respiratory signal indicative of the patient's respiration during the monitoring session and generated with a monitoring device of the plurality of monitoring devices, the respiratory signal derived from at least one sensor;
 computing, in a processor of the system, a stability measure of the patient for a monitoring session, the stability measure representing an indication of a change point having occurred at the monitoring session in a statistical distribution of the respiratory feature; and
 generating by a processor of the system, an output comprising an alert or presentation based on the stability measure, wherein the generating comprises transmitting, via communications over the network, a message for the output, and displaying, on a display device, the alert or presentation in response to the transmitting,
 wherein the chronic respiratory disease state of the patient comprises Chronic Obstructive Pulmonary Disease or a cardio-pulmonary disorder,
 wherein the respiratory feature is a percentile of duration of Cheyne-Stokes respiration cycles,
 wherein the computing forms and analyses a time series of successive values of the extracted respiratory feature indexed by monitoring session identifiers, wherein each monitoring session of the plurality of monitoring sessions is a duration, and wherein the indication is a sum of values of a posterior distribution of run length for the monitoring session given values of the respiratory feature up to and including the monitoring session.

9. A method according to claim 1, wherein the generated alert or presentation is based on a comparison of the stability measure and a threshold.

10. A method according to claim 1, further comprising generating a prompt for the patient to take an action based on a comparison of the stability measure and a threshold.

11. A method according to claim 1, wherein generating the presentation comprises a query to the patient based on a comparison of the stability measure and a threshold.

12. A method according to claim 11, further comprising generating an alert based on a response to the query.

13. A method according to claim 11, further comprising triggering presentation of an additional query to the patient based on a response to the query.

14. A chronic respiratory disease state monitoring apparatus in a system comprising a plurality of monitoring devices and a remote server configured for multi-patient monitoring, the plurality of monitoring devices and the remote server being configured for communications over a network, the chronic respiratory disease state monitoring apparatus comprising:
 a sensor in a monitoring device of the plurality of monitoring devices and configured to generate a respiratory signal indicative of a patient's respiration during a monitoring session; and
 a processor configured to:
 extract, for each of a plurality of monitoring sessions, a respiratory feature from the respiratory signal;
 compute a stability measure of the patient for a monitoring session, the stability measure representing an indication of a change point having occurred at the monitoring session in a statistical distribution of the respiratory feature; and generate an output comprising an alert or presentation based on the stability measure, wherein the generating comprises transmitting, via communications over the network, a message for the output, for displaying, on a display device, the alert or presentation in response to the transmission, wherein the chronic respiratory disease state of the patient comprises Chronic Obstructive Pulmonary Disease or a cardio-pulmonary disorder, wherein to compute the stability measure, the processor is configured to form and analyse a time series of successive values of the extracted respiratory feature indexed by monitoring session identifiers, wherein each monitoring session of the plurality of monitoring sessions is a duration, and wherein the indication is a sum of values of a posterior distribution of run length for the monitoring session given values of the respiratory feature up to and including the monitoring session.

15. The apparatus of claim 14 wherein the stability measure changes (a) to indicate a deterioration in the patient's condition, and (b) to indicate improvement in the patient's condition, and wherein the processor is configured to control generation of the presentation or the alert based on a comparison of the stability measure to a plurality of thresholds.

16. A chronic disease monitoring apparatus according to claim 14, wherein the sensor is a contactless motion sensor and the respiratory signal is a signal representing respiratory movement of the patient.

17. A chronic disease monitoring apparatus according to claim 14, wherein the apparatus is a respiratory pressure therapy device and the respiratory signal is a signal representing respiratory flow rate of the patient from a session with the respiratory pressure therapy device.

18. A non-transitory computer-readable medium containing processor control instructions, which when executed by one or more processors, perform a method of monitoring chronic respiratory disease state of a patient in a system comprising a plurality of monitoring devices and a remote server configured for multi-patient monitoring, the plurality of monitoring devices and the remote server being configured for communications over a network, the processor control instructions comprising:

instructions to extract for each of a plurality of monitoring sessions, a respiratory feature from a respiratory signal indicative of the patient's respiration during the monitoring session and generated with a monitoring device of the plurality of monitoring devices, the respiratory signal derived from at least one sensor; and instructions to compute a stability measure of the patient for a monitoring session, the stability measure representing an indication of a change point having occurred at the monitoring session in a statistical distribution of the respiratory feature, instructions to generate an output comprising an alert or presentation based on the stability measure, wherein the generating comprises transmitting, via communications over the network, a message for the output, and displaying, on a display device, the alert or presentation in response to the transmitting, wherein the chronic respiratory disease state of the patient comprises Chronic Obstructive Pulmonary Disease or a cardio-pulmonary disorder, wherein to compute the stability measure, the instructions to compute are configured to form and analyse a time series of successive values of the extracted respiratory feature indexed by monitoring session identifiers, wherein each monitoring session of the plurality of monitoring sessions is a duration, and wherein the indication is a sum of values of a posterior distribution of run length for the monitoring session given values of the respiratory feature up to and including the monitoring session.

* * * * *